United States Patent
Fukuma et al.

(10) Patent No.: US 11,503,996 B2
(45) Date of Patent: *Nov. 22, 2022

(54) OPHTHALMIC MICROSCOPE AND FUNCTIONALITY ENHANCEMENT UNIT

(71) Applicant: Topcon Corporation, Tokyo (JP)

(72) Inventors: Yasufumi Fukuma, Tokyo (JP); Kazuhiro Oomori, Tokyo (JP)

(73) Assignee: Topcon Corporation, Tokyo (JP)

( * ) Notice: Subject to any disclaimer, the term of this patent is extended or adjusted under 35 U.S.C. 154(b) by 313 days.

This patent is subject to a terminal disclaimer.

(21) Appl. No.: 16/610,259

(22) PCT Filed: May 2, 2018

(86) PCT No.: PCT/JP2018/017568
§ 371 (c)(1),
(2) Date: Feb. 5, 2020

(87) PCT Pub. No.: WO2018/203577
PCT Pub. Date: Nov. 8, 2018

(65) Prior Publication Data
US 2020/0214555 A1   Jul. 9, 2020

(30) Foreign Application Priority Data

| May 2, 2017 | (JP) | JP2017-091997 |
| Aug. 30, 2017 | (JP) | JP2017-165187 |
| Mar. 23, 2018 | (JP) | JP2018-056763 |

(51) Int. Cl.
*A61B 3/10* (2006.01)
*A61B 3/13* (2006.01)

(52) U.S. Cl.
CPC .............. *A61B 3/102* (2013.01); *A61B 3/132* (2013.01)

(58) Field of Classification Search
CPC ............ A61B 3/102; A61B 3/132; A61B 3/13
(Continued)

(56) References Cited

U.S. PATENT DOCUMENTS

| 2012/0092615 A1* | 4/2012 | Izatt | G01B 9/02091 |
| | | | 351/206 |
| 2015/0294468 A1* | 10/2015 | Shimizu | G06T 11/60 |
| | | | 356/479 |

(Continued)

FOREIGN PATENT DOCUMENTS

| JP | 2012-213634 | 11/2013 |
| JP | 2015-519095 | 7/2015 |

(Continued)

OTHER PUBLICATIONS

International Search Report issued in parent PCT Appln. No. PCT/JP2018/017568, dated Jul. 10, 2018.

*Primary Examiner* — Mohammed A Hasan
(74) *Attorney, Agent, or Firm* — BakerHostetler

(57) ABSTRACT

The object of the present invention is to develop an ophthalmologic microscope of a new method that increases the degree of freedom in the optical design in the Galilean ophthalmologic microscope provided with an OCT optical system. The present invention provides an ophthalmologic microscope 1 comprising; an illuminating optical system 300, an observation optical system 400; an objective lens 2; and an OCT optical system 500, characterized in that the optical axis O-500 of the OCT optical system does not penetrate through the objective lens 2, it comprises objective lens for OCT 507 through which the optical axis O-500 of the OCT optical system penetrates, and deflection optical elements 503a, 503b for scanning of the OCT optical system and the objective lens for OCT 507 are in a substantially optically conjugate positional relation.

11 Claims, 17 Drawing Sheets

(58) Field of Classification Search
USPC .......................................................... 351/221
See application file for complete search history.

(56) References Cited

U.S. PATENT DOCUMENTS

2018/0116502 A1* 5/2018 Ishinabe .................. A61B 3/12
2019/0076012 A1* 3/2019 Kobayashi ............. A61B 3/102

FOREIGN PATENT DOCUMENTS

| JP | 2015-205176 | 11/2015 |
| JP | 2017-12429 | 1/2017 |

* cited by examiner

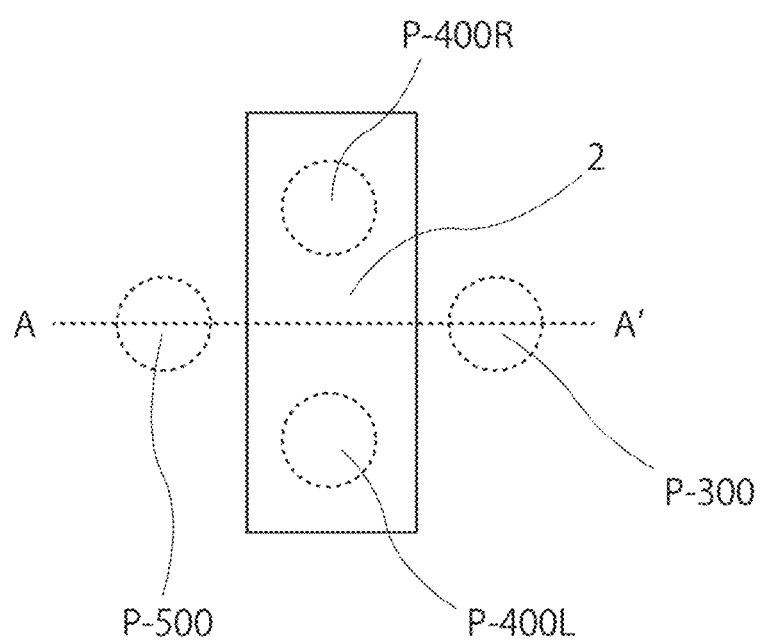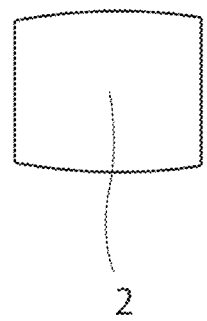
FIG. 12A
FIG. 12B

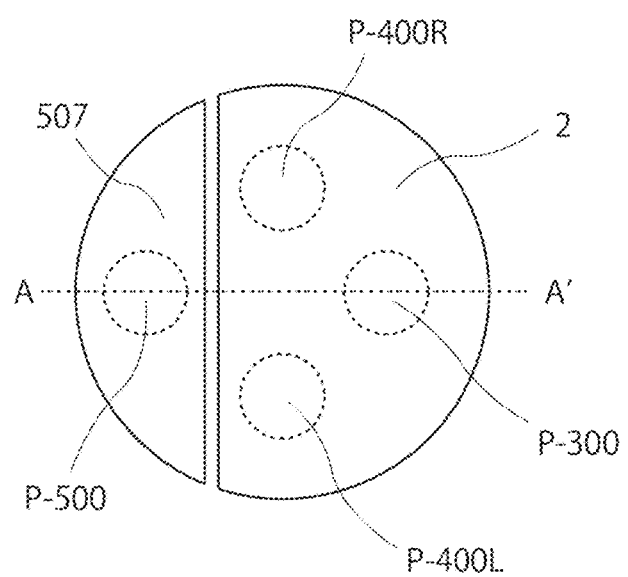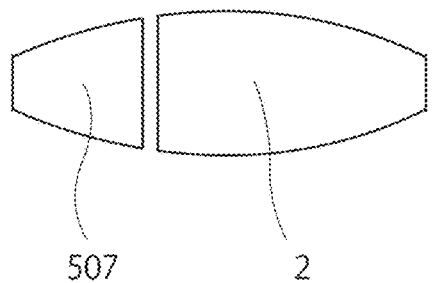
FIG. 15A
FIG. 15B

OPHTHALMIC MICROSCOPE AND FUNCTIONALITY ENHANCEMENT UNIT

RELATED APPLICATIONS

The present U.S. Patent Application is a U.S. national-phase application under 35 U.S.C. § 371 of International Application No. PCT/JP2018/017568, which was filed on May 2, 2018. International Application No. PCT/JP2018/017568 claims priority under 35 U.S.C. § 119 the Paris Convention for the Protection of Industrial Property to Japanese Patent Application Nos. 2017-091997, which was filed on May 2, 2017; Japanese Patent Application No. 2017-165187, which was filed on Aug. 30, 2017; and Japanese Patent Application No. 2018-056763, which was filed Mar. 23, 2018. The entire disclosures for each of the foregoing applications are hereby incorporated by reference.

TECHNICAL FIELD

The present invention relates to an ophthalmologic microscope comprising an illuminating optical system for illuminating a subjects eye and an observation optical system for observing the subjects eye, such as a fundus camera, a slit lamp, a microscope for ophthalmic surgery. The inventive ophthalmologic microscope is characterized in that it comprises an OCT optical system capable of obtaining tomographic images of the subjects eye with Optical Coherence Tomography (abbreviated as OCT) and that the OCT optical system and an observation optical system can be independent from one another, and this can increase the degree of freedom in the design for ophthalmologic microscope.

The invention also relates to a function expansion unit attachable to and detachable from the ophthalmologic microscope and capable of adding functions of OCT to the ophthalmologic microscope.

BACKGROUND ART

An ophthalmologic microscope is a medical or inspection equipment that illuminates a subjects eye of a patient with an illuminating optical system and enlarges it to observe with an observation optical system consisting of lens, etc. Such ophthalmologic microscopes that can obtain tomographic images of the subjects eye due to inclusion of an OCT optical system have been developed.

OCT is a technique that constitutes an interferometer using a low coherence (a short coherence length) light source, thereby obtains tomographic images of a biological body. In particular, it uses the low coherence light source, divides its light in half with a beam splitter, scans one of the lights (a measuring light) with a deflection optical element and irradiates it to the biological tissue to reflect or scatter, and reflects the other of the lights (a reference light) with a mirror. The measuring light is reflected or scattered at a variety of depth of the biological tissue and numerous reflected or scattered light return. After converging the measuring light returned to the beam splitter and the reflected light of the reference light, only the reflected or scattered light of the measuring light which went through the same distance as the reference light is detected interfering with the reflected light of the reference light. Therefore, intensities of the measuring light reflected at the various depth of the biological tissue can be detected by adjusting positions of the beam splitter and the mirror to variously change the path length of the reference light. With such OCT optical system, tomographic images of a biological tissue can be obtained.

Providing this OCT optical system on an ophthalmologic microscope enabled to obtain tomographic images of a retina and cornea of eye, iris, etc. and enabled to observe not only the surface but also internal condition of tissues. This can improve diagnostic accuracy of eye diseases, and also improve the success rate in ophthalmic surgery.

For the ophthalmologic microscope comprising such OCT optical system, there is a need to incorporate the OCT optical system into the microscope comprising the illuminating optical system and the observation optical system such that the light of the OCT optical system can enter a subject's eye, and various methods have been developed.

For example, for a Galilean ophthalmologic microscope that comprises an observation optical system consisting of observation optical systems for left and right eyes of an observer, and comprises one objective lens through which the optical axes of the observation optical systems for left and right eyes commonly penetrate, there is a method that makes the light of OCT light source entered from the side of the objective lens reflect directly on the objective lens with a reflecting member and then penetrate through the objective lens to enter the subjects eye (Patent documents 1 and 2, etc.).

Explaining more fully, as shown in FIG. 16 (a drawing cited from FIG. 1 of Patent document 1), the ophthalmologic microscope comprises an observation optical system consisting of lens groups 130, 140, 150, 170, 180, that are pairs of left and right through which the optical axis of the observation optical system for left eye and the optical axis of the observation optical system for right eye penetrate respectively, one objective lens 110 through which the optical axis of the observation optical system for left eye and the optical axis of the observation optical system for right eye commonly penetrate, OCT optical systems 200, 250, 450, 460, 470, and illuminating optical systems 310, 320, 330. In the OCT optical system, the output light from the OCT light source 200 is emitted through an optical fiber 250, converged with the illuminating light from the illuminating optical system at a beam combiner 340 after being controlled its direction by two scanning mirrors 450, 460, and reflected at beam splitter 120 to enter a subjects eye 1000.

Yet, for the Galilean ophthalmologic microscope, there is a method that makes the light of the OCT light source emit from the upper side of the objective lens, penetrate through the objective lens, and enter a subjects eye (Patent document 3).

Moreover, for the Galilean ophthalmologic microscope, there is a method that makes the light path of the OCT optical system converge substantially coaxially with the light path of the observation optical system, penetrate the objective lens, and enter a subjects eye (Patent documents 4 and 5).

All methods described above are ones that the optical axis of the observation optical system and the optical axis of the OCT optical system commonly penetrate through one objective lens.

For the Galilean ophthalmologic microscope, as a method that the optical axis of the OCT optical system does not penetrate through objective lens, there is a method that makes the light of OCT light source entered from the side of the objective lens reflect directly under the objective lens with a deflection member, and enter a subjects eye without penetrating through the objective lens (Patent documents 6 and 7).

Explaining more fully, in the ophthalmologic microscope shown in FIG. 17 (a drawing cited from FIG. 3 of Patent document 7), at the lower side of the objective lens 15 through which the optical axis of the observation optical system penetrates, the light of the OCT light source entered from the side of the objective lens 15 is reflected at the deflection member 106, and the light of the OCT optical system enters a subjects eye. In this ophthalmologic microscope, it has been shown the position (for example, intermediate position) between the first scanner 102a and the second scanner 102b which are deflection optical elements for scanning and the position of the subject eye E are substantially optically conjugate (paragraph [0043] in Patent document 7).

Also, as a method different from the Galilean ophthalmologic microscope, there is a Greenough ophthalmologic microscope that comprises two objective lenses corresponding to the left and right observation optical systems, respectively, and sets the stereo angle between the left and right observation optical systems (Patent documents 8 and 9). In the Greenough ophthalmologic microscope, since there is no objective lens through which the optical axes of the left and right observation optical systems commonly penetrate, the light path of the OCT optical system can enter a subjects eye without penetrating through the objective lens. However, the Greenough ophthalmologic microscope requires a complex optical design in order to incline the left and right observation optical systems each other to set the stereo angle.

PRIOR ART REFERENCES

Patent Documents

[Patent document 1] JP 8-66421 A
[Patent document 2] JP 2008-264488 A
[Patent document 3] JP 2008-268852 A
[Patent document 4] JP 2010-522055 A
[Patent document 5] JP 2008-264490 A
[Patent document 6] U.S. Pat. No. 8,366,271 B
[Patent document 7] JP 2016-206348 A
[Patent document 8] JP 2016-185177 A
[Patent document 9] JP 2016-185178 A

DISCLOSURE OF THE INVENTION

Problems to be Solved by the Invention

As described above, for the conventional ophthalmologic microscopes provided with the OCT optical system, there exist the Galilean ophthalmologic microscope and the Greenough ophthalmologic microscope, however, the latter has required a complex optical design.

Also, for the conventional Galilean ophthalmologic microscope, although many methods that the optical axis of the observation optical system and the optical axis of the OCT optical system commonly penetrate through one objective lens have been developed as indicated in Patent documents 1 to 5, etc., the degree of freedom in the optical design is limited because the OCT optical system and the observation optical system are influenced by each other as they are not independent from one another.

For the conventional Galilean ophthalmologic microscope, although the method that the optical axis of the OCT optical system does not penetrate through the objective lens has been developed as indicated in Patent documents 6 and 7, there is a problem that it is not able to secure enough distance between the ophthalmologic microscope and a subjects eye, because of the optical members of the OCT optical system provided between the objective lens and the subjects eye.

Thus, in light of the conventional situation above, the object of the present invention is to develop, for the Galilean ophthalmologic microscope provided with OCT optical system, an ophthalmologic microscope of a new method that increases the degree of freedom in the optical design.

Means for Solving the Problems

As a result of the keen research in order to solve the problems above, the inventors found that, for the Galilean ophthalmologic microscope, the observation optical system and the OCT optical system become independent from one another by placing them in such a way the optical axis of the OCT optical system does not penetrate through the objective lens through which the optical axis of the observation optical system penetrates and providing an objective lens for OCT aside from the objective lens, which leads to increased degree of freedom in the optical design. And we came to complete the present invention with a finding that it is possible to scan the measuring light in a wide irradiation range even with an objective lens for OCT of small aperture by placing a deflection optical element for scanning of the OCT optical system and the objective lens for OCT so that they are in a substantially optically conjugate positional relation.

That is, the present invention provides the first invention below regarding an ophthalmologic microscope, the second invention below regarding a function expansion unit, and the third invention below regarding a function expansion set.

(1) The first invention relates to an ophthalmologic microscope comprising:
an illuminating optical system for illuminating a subjects eye;
an observation optical system that comprises an observation optical system for left eye and an observation optical system for right eye to observe the subjects eye illuminated by the illuminating optical system;
an objective lens through which the optical axis of the observation optical system for left eye and the optical axis of the observation optical system for right eye of the observation optical system commonly penetrate; and
an OCT optical system comprising a light path of a measuring light for testing the subject's eye by Optical Coherence Tomography and a deflection optical element that scans the measuring light,
characterized in that the observation optical system, the objective lens, and the OCT optical system are placed in such a way that the optical axis of the OCT optical system does not penetrate through the objective lens through which the optical axis of the observation optical system penetrates, it comprises, aside from the objective lens, an objective lens for OCT through which the optical axis of said OCT optical system penetrates, wherein the deflection optical element and the objective lens for OCT are in a substantially optically conjugate positional relation.

(2) It is preferable that the OCT optical system comprises:
a first optical member that guides a light from an OCT light source to a first optical axis direction;
a first reflecting member that guides the light guided to the first optical axis direction to a second optical axis direction substantially perpendicular to the first optical axis direction;
a second optical member that relays the light guided to the second optical axis direction; and a second reflecting member that guides the light relayed by the second optical member to a third optical axis direction substantially perpendicular to the second optical axis direction, wherein the objective lens for OCT is placed on the third optical axis so as to irradiate a prescribed section of the subjects eye with the light guided to the third optical axis direction.

(3) In the ophthalmologic microscope of the first invention, it is preferable that, when the deflection optical element consists of a pair of two deflection optical elements that scan in a different direction, it comprises a relay optical system on the light path between the two deflection optical elements, and both of the two deflection optical elements are in a substantially optically conjugate positional relation with the objective lens for OCT.

(4) In any of ophthalmologic microscopes above, it is preferable that the objective lens has a partial shape of circular lens or a shape of circular lens with a cutout or hole, wherein the optical axis of the OCT optical system penetrates through a portion where the objective lens does not exist, or through the cutout or hole provided in the objective lens.

(5) In any of the ophthalmologic microscopes above, a circular lens or a lens consisting of part of a circular lens can be divided in two, with one of the divided lenses being as the objective lens and the other being as an objective lens for OCT.

(6) In any of ophthalmologic microscopes above, it is preferable to further comprise an objective lens position control mechanism that adjusts the position of the objective lens or the objective lens for OCT.

(7) In any of ophthalmologic microscopes above, it is preferable that the OCT optical system is detachably unitized.

(8) In any of ophthalmologic microscopes above, it is preferable to further comprise a detachable front-end lens onto a light path between the subjects eye and the objective lens to observe a retina of the subjects eye.

(9) The second invention relates to a function expansion unit used for an ophthalmologic microscope comprising: an illuminating optical system for illuminating a subjects eye, an observation optical system that comprises an observation optical system for left eye and an observation optical system for right eye to observe the subjects eye illuminated by the illuminating optical system, and an objective lens through which the optical axis of the observation optical system for left eye and the optical axis of the observation optical system for right eye of the observation optical system commonly penetrate, characterized in that the function expansion unit comprises:

a joint attachable to and detachable from the ophthalmologic microscope; and an OCT optical system comprising a light path of a measuring light for testing the object's eye by Optical Coherence Tomography, a deflection optical element that scans the measuring light, and an objective lens for OCT, wherein the optical axis of the OCT optical system does not penetrate through the objective lens but penetrates through the objective lens for OCT when the function expansion unit is attached to the ophthalmologic microscope via the joint, and wherein the deflection optical element and the objective lens for OCT are in a substantially optically conjugate positional relation.

(10) In the function expansion unit of the second invention, it is preferable that the OCT optical system comprises:

a first optical member that guides a light from an OCT light source to a first optical axis direction;

a first reflecting member that guides the light guided to the first optical axis direction to a second optical axis direction substantially perpendicular to the first optical axis direction;

a second optical member that relays the light guided to the second optical axis direction; and a second reflecting member that guides the light relayed by the second optical member to a third optical axis direction substantially perpendicular to the second optical axis direction, wherein the objective lens for OCT is placed on the third optical axis so as to irradiate a prescribed section of the subjects eye with the light guided to the third optical axis direction.

(11) In any of function expansion units above, when the deflection optical element consists of a pair of two deflection optical elements that scan in a different direction, it comprises a relay optical system on the light path between the two deflection optical element, wherein both of the two deflection optical elements are in a substantially optically conjugate positional relation with the objective lens for OCT.

(12) In any of function expansion units above, it is preferable to further comprise a detachable front-end lens onto a light path between the subjects eye and the objective lens to observe a retina of the subjects eye.

(13) The third invention provides a function expansion set characterized in that it comprises any of function expansion units above and an objective lens for replacement to replace the objective lens.

(14) In the third invention, it is preferable that the objective lens for replacement has a partial shape of circular lens or a shape of circular lens with a cutout or hole, wherein when replacing the objective lens with the objective lens for replacement and attaching the function expansion unit to the ophthalmologic microscope via the joint, the optical axis of the OCT optical system penetrates through a portion where the objective lens for replacement does not exist, or through the cutout or hole provided in the objective lens for replacement.

Effect of the Invention

In the ophthalmologic microscope of the first invention, the optical axis of the observation optical system penetrates through the objective lens while the optical axis of the OCT optical system penetrates through the objective lens for OCT which has been provided aside from the objective lens. With this configuration, the ophthalmologic microscope of the present invention is one which the observation optical system and the OCT optical system are independent from one another. Therefore, the ophthalmologic microscope of the present invention can perform optical design without the observation optical system and the OCT optical system being influenced each other and thus it is effective in increasing the degree of freedom in the optical design. The ophthalmologic microscope of the present invention is also effective in being able to scan the measuring light in a wide irradiation range even with an objective lens for OCT of small aperture because the deflection optical element for scanning of the OCT optical system and the objective lens for OCT are in a substantially optically conjugate positional relation.

For the function expansion unit of the second invention and the function expansion set of the third invention, the optical axis of the observation optical system for the ophthalmologic microscope penetrates through the objective lens while the optical axis of the OCT optical system for the function expansion unit does not penetrate through the objective lens but penetrates through the objective lens for OCT. With this configuration, the OCT optical system for the function expansion unit is independent from the observation optical system for the ophthalmologic microscope, thereby allows for unitization and is also effective in increasing the degree of freedom in the optical design. As the function expansion unit is attachable to and detachable from the ophthalmologic microscope via a joint, the function expansion unit and the function expansion set of the present invention are effective in readily adding functions of OCT to the ophthalmologic microscope. Also, the function expansion unit and the function expansion set of the present invention is effective in being able to scan the measuring light in a wide irradiation range even with an objective lens for OCT of small aperture because the deflection optical element for scanning of the OCT optical system and the objective lens for OCT are in a substantially optically conjugate positional relation.

BRIEF DESCRIPTION OF THE DRAWINGS

FIG. 4 (A) is a view from the direction of the optical axis of the objective lens and FIG. 4 (B) is a cross-sectional view in the plane including the line AA' of FIG. 4 (A).

FIG. 11 (A) illustrates an objective lens seen from the optical axis direction and FIG. 11 (B) is a cross-sectional view in the plane including a line AA' of FIG. 11 (A).

FIG. 12 schematically illustrates a shape of an objective lens used for the ophthalmologic microscope of the fourth embodiment of the present invention. FIG. 12(A) is a view from the direction of the optical axis of the objective lens and FIG. 12 (B) is a cross-sectional view in the plane including a line AA' of FIG. 12 (A).

FIG. 14 (A) is a view from the direction of the optical axis of the objective lens and FIG. 14 (B) is a cross-sectional view in the plane including a line AA' of FIG. 14 (A).

FIG. 15 schematically illustrates shapes of an objective lens and an objective lens for OCT used for the ophthalmologic microscope of the seventh embodiment of the present invention. FIG. 15 (A) is a view from the direction of the optical axis of the objective lens and FIG. 15 (B) is a cross-sectional view in the plane including a line AA' of FIG. 15 (A).

DESCRIPTION OF EMBODIMENTS

Figure 1:
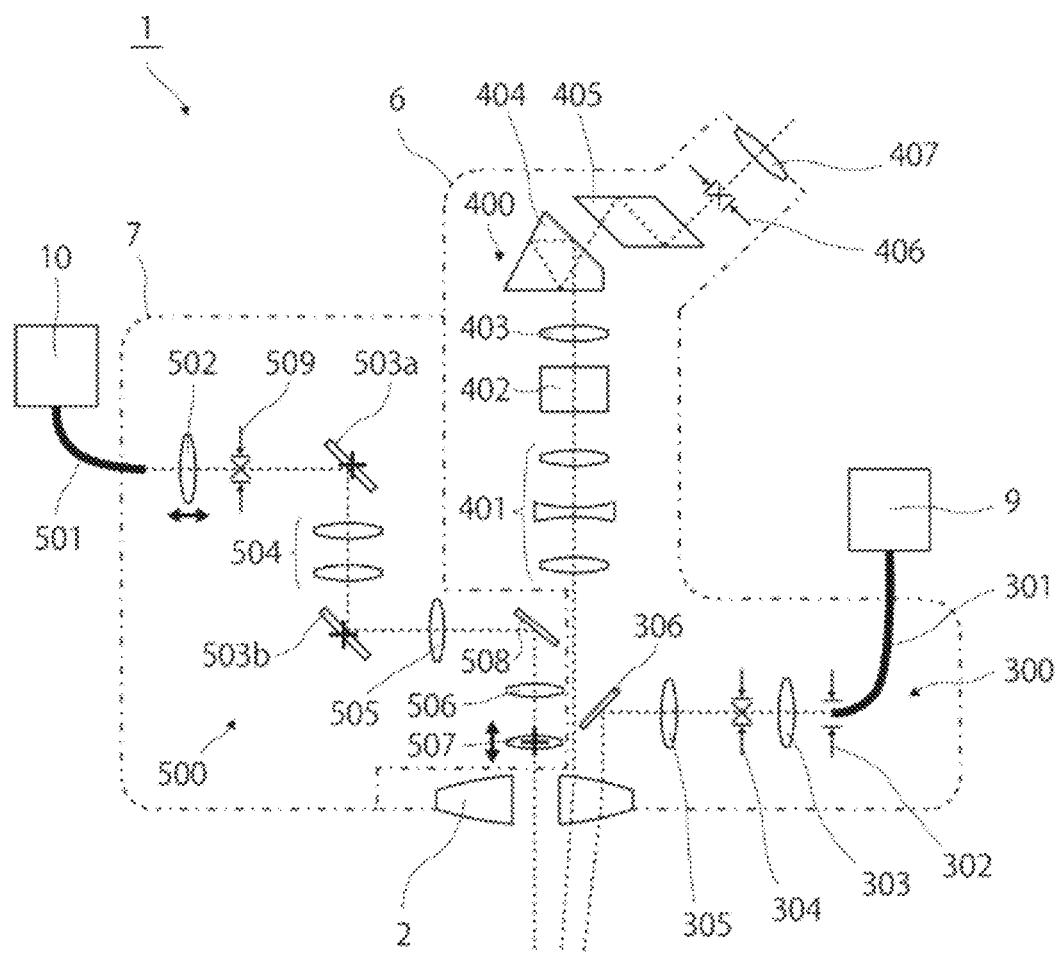
FIG. 1 schematically illustrates the configuration of an optical system taken from a side view, regarding to the ophthalmologic microscope of the first embodiment of the present invention.
Figure 1:
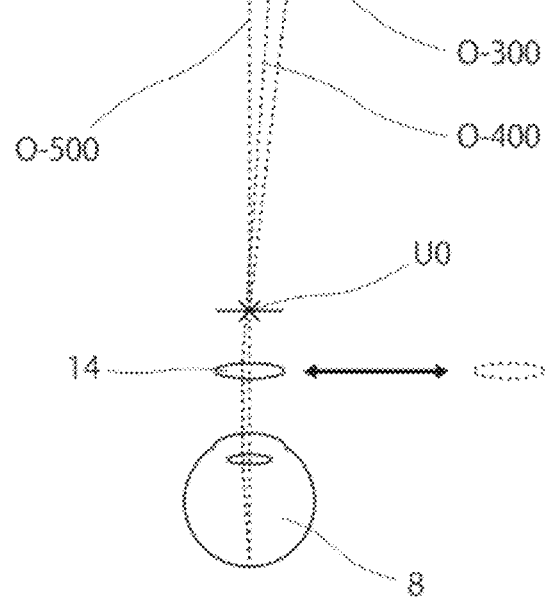

1. Ophthalmologic Microscope 1-1 Summary of the Ophthalmologic Microscope of the Present Invention The ophthalmologic microscope of the present invention relates to an ophthalmologic microscope comprising: an illuminating optical system for illuminating a subjects eye; an observation optical system that comprises an observation optical system for left eye and an observation optical system for right eye to observe the subjects eye illuminated by the illuminating optical system; an objective lens through which the optical axis of the observation optical system for left eye and the optical axis of the observation optical system for right eye of the observation optical system commonly penetrate, and an OCT optical system including a deflection optical element that scans a light path of a measuring light for testing the subjects eye and the measuring light with Optical Coherence Tomography.

For the ophthalmologic microscope of the present invention, the observation optical system, the objective lens, and the OCT optical system are placed in such a way that the optical axis of the OCT optical system does not penetrate through the objective lens through which the optical axis of the observation optical system penetrates, and it comprises, aside from the objective lens, an objective lens for OCT through which the optical axis of the OCT optical system. With this configuration, the ophthalmologic microscope of the present invention is one which the observation optical system and the OCT optical system are independent from one another.

Therefore, in the ophthalmologic microscope of the present invention, as it is possible to perform optical design without the observation optical system and the OCT optical system being not influenced each other, the ophthalmologic microscope of the present invention is effective in increasing the degree of freedom in the optical design.

For example, but not limited to, controlling the position of the objective lens and the objective lens for OCT independently allows for an optical design that adjusts the observation focus of the observation optical system (observation focus plane) and the focus of the OCT optical system (OCT scanning plane) independently. It also allows for an optical design that separates the OCT optical system from the observation optical system to make the OCT optical system an attachable unit to and detachable unit from the ophthalmologic microscope. Furthermore, it allows for an optical design that can obtain 3D tomographic images in more detail by adding not only one but also a plurality of OCT optical systems to the ophthalmologic microscope.

The ophthalmologic microscope of the present invention is characterized in that the deflection optical element for scanning and the objective lens for OCT are in a substantially optically conjugate positional relation. This is effective in being able to scan the measuring light in a wide irradiation range even with an objective lens for OCT of small aperture.

Here, "being in a substantially optically conjugate positional relation" means that the deflection optical element and the objective lens for OCT are respectively located at two conjugate positions on the optical axis or their anteroposterior positions. Also, "conjugate positional relation" means a positional relation that when an image is formed on the one side, the same image is formed on the other side as well.

In the ophthalmologic microscope of the present invention, there may be one or two or more deflection optical elements for scanning of the OCT optical system. When using two or more deflection optical elements, at least one of the deflection optical elements may be in a substantially optically conjugate positional relation with the objective lens for OCT.

When using two deflection optical elements, it is possible to two-dimensionally scan the measuring light by having one deflection optical element as a deflection optical element for scanning in x-axis direction and the other as a deflection optical element for scanning in y-axis direction, for example.

In this case, with the deflection optical element for scanning in x-axis direction and the objective lens for OCT being in a substantially optically conjugate positional relation, it is possible to keep the scan width in x-axis direction large even with the objective lens for OCT of small aperture. In addition, with the deflection optical element for scanning in y-axis direction and the objective lens for OCT being in a substantially optically conjugate positional relation, it is possible to keep the scan width in y-axis direction large even with the objective lens for OCT of small aperture. Preferably, both of the deflection optical elements for scanning in x-axis direction and y-axis direction may be in a substantially optically conjugate positional relation with the objective lens for OCT.

When using a pair of two deflection optical elements that scan in a different direction as deflection optical elements, providing a relay optical system on the light path between the two deflection optical elements allows to perform optical design such that both of the two deflection optical elements are in a substantially optically conjugate positional relation with the objective lens for OCT.

Here, the relay optical system may be any optical system that is an optical element such as lens and provided between two deflection optical elements, for example, may be a lens group consisting of two or more lens.

If the distance between two deflection optical elements is less than 20 mm and the intermediate position of the two deflection optical elements is a position conjugate to the objective lens for OCT, both of the two deflection optical elements can be in a substantially optically conjugate positional relation with the objective lens for OCT without using said relay optical system.

In the present invention, "ophthalmologic microscope" refers to a medical or inspection equipment that can enlarge a subject's eye to observe, and it encompasses one not only for human but also for animal "Ophthalmologic microscope" includes, for example, but not limited to, a fundus camera, a slit lamp, a microscope for ophthalmic surgery, etc.

In the present invention, "illuminating optical system" is configured to include an optical element for illuminating a subject's eye. The illuminating optical system may further include a light source, but it may guide natural light to a subject's eye. Also, in the present invention, "observation optical system" is configured to include an optical element that can observe a subjects eye with return light which is reflected/scattered from the subjects eye illuminated by the illuminating optical system.

In the present invention, the observation optical system comprises an observation optical system for left eye and an observation optical system for right eye, so it is possible to observe stereoscopically with binocular vision when generating a parallax in the image obtained by the left and right observation optical systems.

Also, "observation optical system" of the present invention may directly observe a subjects eye through an eyepiece lens, etc., may observe it by accepting a light with an imaging element, etc., for imaging, or may be provided with both functions.

In the present invention, "OCT optical system" is configured to include an optical element that the measuring light of the OCT passes through and a deflection optical element that scans the measuring light. The OCT optical system may further include an OCT light source.

In the present invention, "deflection optical element" may be any optical element that can change the direction of light and scan the light. For example, but not limited to, an optical element comprising a reflection portion that its orientation changes, like a galvano mirror, a polygon mirror, a rotation mirror, a MEMS (Micro Electro Mechanical Systems) mirror, etc., and an optical element that can changes the direction of light with an electric field or acoustic-optic effects, like a deflection prism scanner and an AO element, can be employed.

In the present invention, as an optical element used in "illuminating optical system", "observation optical system", "OCT optical system", for example, but not limited to, a lens, a prism, a mirror, a light filter, a diaphragm, a diffraction grating, a polarizing element, etc. can be used.

In the present invention, "objective lens" or "objective lens for OCT" is a lens in the ophthalmologic microscope, which are provided at the side of a subject's eye. "Objective lens" of the present invention does not include a front-end lens (loupe) inserted between an objective lens and a subject's eye to use.

Although "objective lens" in the present invention is an objective lens through which the optical axis of the observation optical system for left eye and the optical axis of the observation optical system for right eye commonly penetrate, the optical axis of the OCT optical system does not penetrate through the objective lens, as mentioned above. Also, the optical axis of the illuminating optical system may or may not penetrate through the objective lens. An additional objective lens for illuminating can be provided when the optical axis of the illuminating optical system does not penetrate through the objective lens.

1-2. First Embodiment

Figure 2:
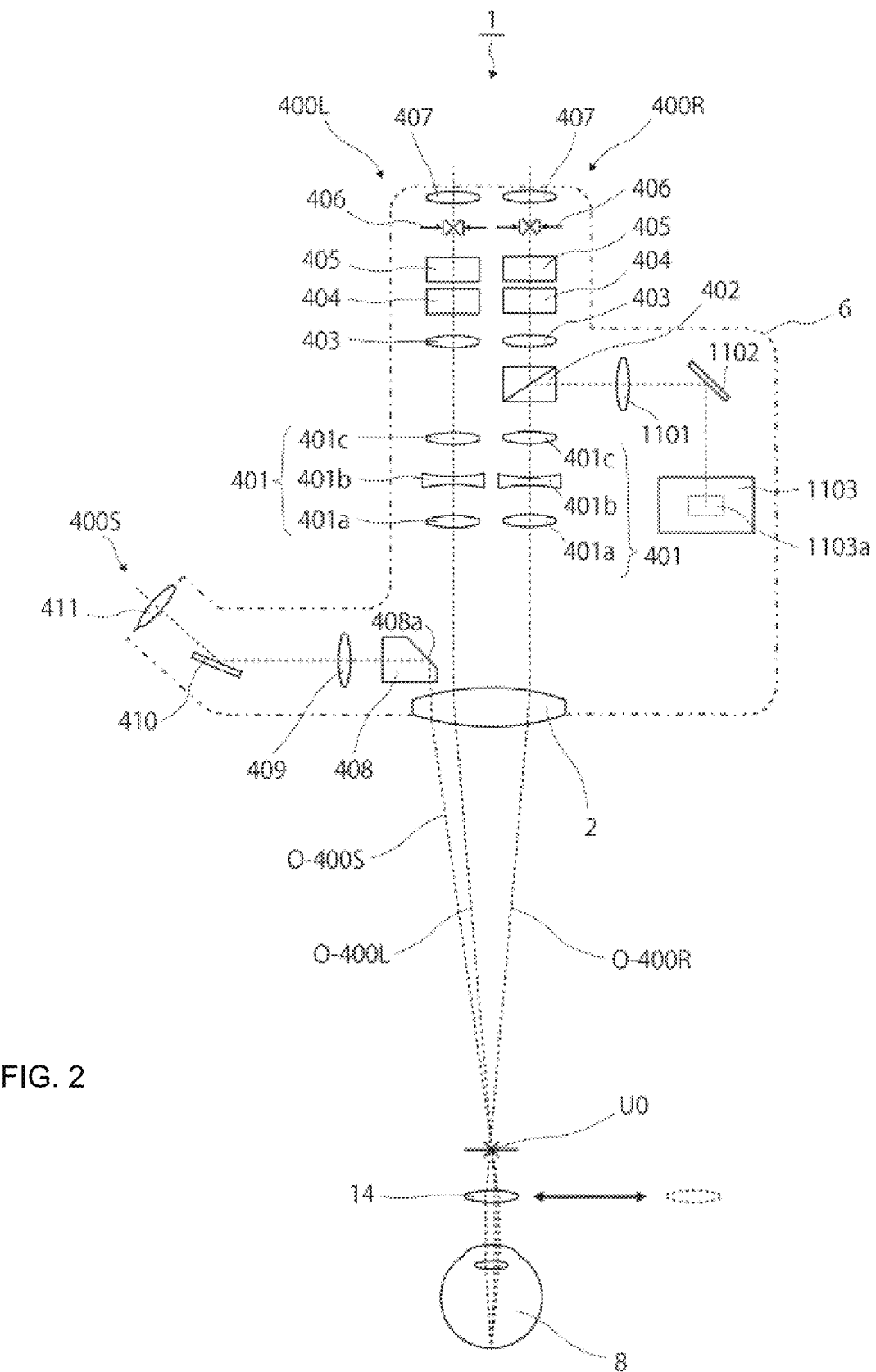
FIG. 2 schematically illustrates the configuration of an optical system taken from a front view, regarding to the ophthalmologic microscope of the first embodiment of the present invention.
Figure 3:
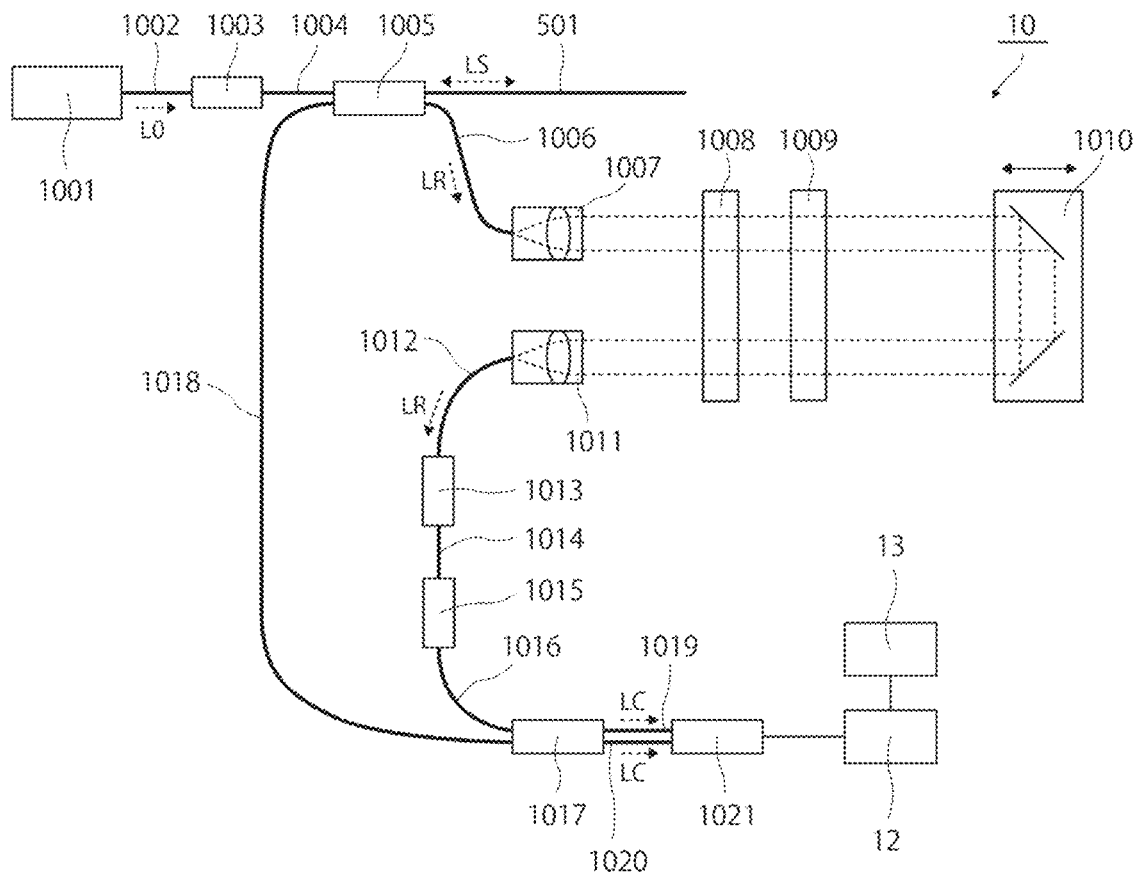
FIG. 3 schematically illustrates the optical configuration of an OCT unit used in the ophthalmologic microscope of the first embodiment of the present invention.
Figure 4A:
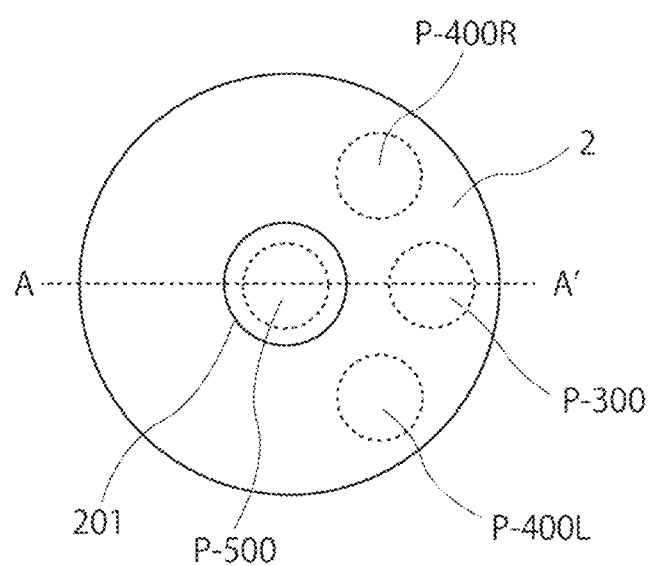
FIG. 4 schematically illustrates a shape of an objective lens used for the ophthalmologic microscope of the first embodiment of the present invention.
Figure 4B:
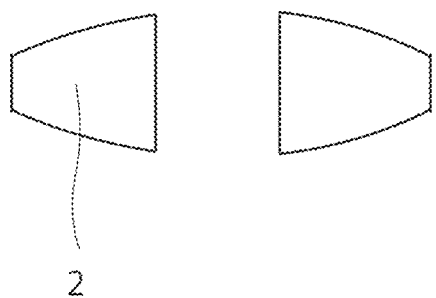

Hereinafter, examples of the embodiments of the present invention will be fully described in reference to drawings. FIGS. 1-4 schematically illustrate the first embodiment which is an example of the ophthalmologic microscope of the present invention. FIG. 1 is a schematic diagram from a side view of the configuration of an optical system for the ophthalmologic microscope of the first embodiment, and FIG. 2 is a schematic diagram from a front view. Also, FIG. 3 schematically illustrates the optical configuration of an OCT unit, and FIG. 4 schematically illustrates a shape of objective lens.

As shown in FIG. 1, the optical system of the ophthalmologic microscope 1 comprises an objective lens 2, an illuminating optical system 300, an observation optical system 400, and an OCT optical system 500.

The objective lens 2, the illuminating optical system 300, and the observation optical system 400 are accommodated in an ophthalmologic microscope body 6. On the other hand, the OCT optical system 500 is accommodated in a function expansion unit 7. In FIG. 1, the ophthalmologic microscope body 6 and the function expansion unit 7 are respectively indicated by dashed-dotted lines.

The ophthalmologic microscope body 6 and the function expansion unit 7 are detachably coupled by a joint (not shown).

As shown in FIG. 1, the illuminating optical system 300 illuminates subjects eye 8 through the objective lens 2. The illuminating optical system 300 is configured to include an illuminating light source 9, an optical fiber 301, an emission opening diaphragm 302, a condenser lens 303, an illuminating field diaphragm 304, a collimating lens 305, and a reflecting mirror 306. The optical axis of the illuminating optical system 300 is indicated by a dotted line O-300 in FIG. 1.

The illuminating light source 9 is provided outside of the ophthalmologic microscope body 6. The illuminating light source 9 is connected to one end of the optical fiber 301. The other end of the optical fiber is placed at the position facing the condenser lens 303 inside of the ophthalmologic microscope body 6. The illuminating light output from the illuminating light source 9 is guided by the optical fiber 301 to enter the condenser lens 303.

The emission opening diaphragm 302 is provided at the position facing the emission opening of the optical fiber 301 (fiber end at the condenser lens 303). The emission opening diaphragm 302 functions so as to block a partial region of the emission opening of the optical fiber 301. Once the blocked region is changed by the emission opening diaphragm 302, the emission region of illuminating light is changed. Thereby, the irradiation angle of the illuminating light, that is, an angle between the incident direction of the illuminating light against subjects eye 8 and the optical axis of the objective lens 2 can be changed.

The illuminating field diaphragm 304 is provided at the position optically conjugate to the front side focal position U0 of the objective lens 2 (the position of X). The collimating lens 305 converts the illuminating light that passed through the illuminating field diaphragm 304 into a parallel light flux. The reflecting mirror 306 reflects the illuminating light converted into a parallel light flux by the collimating lens 305, towards the objective lens 2. The reflected light is irradiated towards the subjects eye 8 through the objective lens 2. (A part of) the illuminating light irradiated towards the subjects eye 8 is reflected/scattered at the tissue of the subjects eye, such as a cornea and retina.

That reflected/scattered return light (also referred as "observed light") penetrates through the objective lens 2 and enters the observation optical system 400.

As shown in FIG. 1, the observation optical system 400 is configured to include a variable magnification lens system 401, a beam splitter 402, an imaging lens 403, an image erecting prism 404, an eye width adjusting prism 405, a field diaphragm 406, and an eyepiece lens 407. The optical axis of the observation optical system 400 is indicated by a dotted line O-400 in FIG. 1.

The observation optical system 400 is used to observe the subjects eye 8, which is being illuminated by the illuminating optical system 300, via the objective lens 2.

As shown in FIG. 1, the OCT optical system 500 is configured to include an OCT unit 10, an optical fiber 501, a collimating lens 502, an illuminating field diaphragm 509, a scanning mirror 503a, 503b, a relay optical system 504, a first lens group 505, a reflecting mirror 508, a second lens group 506, and an objective lens for OCT 507.

The optical axis of the OCT optical system 500 is indicated by a dotted line O-500 in FIG. 1.

As shown in FIG. 1, in the first embodiment, a hole is provided in the center of the objective lens 2. The optical axis O-500 of the OCT optical system does not penetrate through the objective lens as it penetrates through the hole of the objective lens 2. The optical axis O-500 of the OCT optical system penetrates through the objective lens for OCT 507. With this, the OCT optical system and the observation optical system are independent from one another.

The OCT unit 10 divides the light from a low coherence (short coherence length) OCT light source into a measuring light and a reference light. The measuring light is guided by the OCT optical system 500 and irradiated towards the subjects eye 8, then it reflects/scatters at the tissue of the subjects eye and becomes a return light to be guided to the OCT unit 10. The interference between the return light and the reference light of the measuring light is detected at the OCT unit 10. This allows to obtain tomographic images of the tissue of the subjects eye.

As shown in FIG. 1, the OCT unit 10 is provided outside of the function expansion unit 7 but coupled with it by being connected to the one end of the optical fiber 501. The measuring light generated by the OCT unit 10 emits from the other end of the optical fiber 501. The emitted measuring light is irradiated towards the subjects eye 8 by way of the collimating lens 502, the illuminating field diaphragm 509, the scanning mirror 503a, 503b, the relay optical system 504, the first lens group 505, the reflecting mirror 508, the second lens group 506, the objective lens for OCT 507, etc., and the return light of the measuring light reflected/scattered at the tissue of the subjects eye 8 travels the same pathway in opposite direction and enters the other end of the optical fiber 501.

When observing a retina at the fundus of the eye, the front-end lens 14 is inserted onto optical axes O-300, O-400, O-500 right in front of the subjects eye by a moving mean (not shown). In this case, the front side focal position U0 of the objective lens 2 is conjugate to the retina at the fundus of eye.

Also, when observing an anterior eye part such as a cornea, an iris, etc., the observation is performed by eliminating the front-end lens from right in front of the subjects eye.

As shown in FIG. 1, the collimating lens 502 converts the measuring light emitted from the other end of the optical fiber 501 into a parallel light flux. The collimating lens 502 and the other end of the optical fiber 501 are configured to be relatively movable along the optical axis of the measuring light. In the first embodiment, the collimating lens 502 is configured to be movable, but the other end of the optical fiber 501 may be configured to be movable along the optical axis of the measuring light.

The illuminating field diaphragm 509 is conjugate to the front side focal position U0 of the objective lens for OCT 507.

The scanning mirrors 503a, 503b in the OCT optical system are deflection optical elements that two-dimensionally deflect the measuring light converted into a parallel light flux by the collimating lens 502. The scanning mirror is a galvano mirror that includes a first scanning mirror 503a comprising a deflection plane rotatable around x-axis and a second scanning mirror 503b comprising a deflection plane rotatable around y-axis orthogonal to x-axis. The relay optical system 504 is provided between the first scanning mirror 503a and the second scanning mirror 503b.

By providing only the first scanning mirror 503a as a deflection optical element for scanning and rotating it about x-axis to irradiate with the measuring light, it is possible to scan the irradiation region linearly along y-axis. However, since the measuring light penetrates through the objective lens for OCT 507, the scan range is restricted by the size (aperture) of the objective lens for OCT 507.

Here, if the first scanning mirror 503a and the objective lens for OCT 507 are in a substantially optically conjugate positional relation, it is possible to reduce the restriction imposed by the size (aperture) of the objective lens for OCT 507 and ensure a wide scan range even with the objective lens for OCT of small aperture.

Also, by providing only the second scanning mirror 503b as a deflection optical element for scanning and rotating it about y-axis to irradiate with the measuring light, it is possible to scan the irradiation region linearly along x-axis. However, since the measuring light penetrates through the objective lens for OCT 507, the scan range of the measuring light is restricted by the size (aperture) of the objective lens for OCT 507.

Here, if the second scanning mirror 503b and the objective lens for OCT 507 are in a substantially optically conjugate positional relation, it is possible to reduce the restriction imposed by the size (aperture) of the objective lens for OCT 507 and ensure a wide scan range even with the objective lens for OCT of small aperture.

As shown in FIG. 1, in the first embodiment of the present invention, by having the first scanning mirror 503a and the second scanning mirror 503b as the deflection optical elements for scanning and rotating both of them to irradiate with the measuring light, it is possible to make the irradiation region have a stretch in two direction of x-axis and y-axis. However, since the measuring light penetrates through the objective lens for OCT 507, the irradiation region of the measuring light is restricted by the size (aperture) of the objective lens for OCT 507.

In the ophthalmologic microscope of the first embodiment, a relay optical system 504 is provided between the first scanning mirror 503a and the second scanning mirror 503b. Both of the first scanning mirror 503a and the second scanning mirror 503b are in an optically conjugate positional relation with the objective lens for OCT 507. In FIG. 1, the sections in an optically conjugate positional relation are indicated by symbol +.

Having such conjugate positional relation, in the ophthalmologic microscope of the first embodiment, it is possible to reduce the restriction imposed by the size (aperture) of the objective lens for OCT 507 and have a wide irradiation region even with an objective lens for OCT of small aperture.

The first lens group 505 shown in FIG. 1 is configured to include one or more lenses. The second lens group 506 also configured to include one or more lenses. Moreover, the objective lens for OCT 507 is provided on the side facing the subjects eye 8.

The objective lens for OCT is configured to be movable along the optical axis, so it is possible to adjust the focus of the OCT optical system by controlling the position of the objective lens for OCT. This allows to adjust the focus of the OCT optical system to the position different from the focus of the observation optical system.

Thus, in the ophthalmologic microscope of the first embodiment, since the optical axis of the OCT optical system O-500 does not penetrate through the objective lens 2 but penetrates through the objective lens for OCT 507, the observation optical system and the OCT optical system are independent from one another.

Therefore, in the ophthalmologic microscope of the first embodiment, it is possible to control the observation optical system and the OCT optical system independently, and it is also possible to have the OCT optical system as a unit attachable to and detachable from the ophthalmologic microscope.

The ophthalmologic microscope of the first embodiment further will be further fully described in reference to drawings.

FIG. 2 is a schematic diagram from a front view of the configuration of an optical system for the ophthalmologic microscope of the first embodiment.

As shown in FIG. 2, the observation optical system is separated into observation optical systems for left eye 400L and for right eye 400R of an observer, each comprising an observation light path. The optical axes of the left and right observation optical systems are indicated by dotted lines O-400L, O-400R, respectively, in FIG. 2.

As shown in FIG. 2, the left and right observation optical systems 400L, 400R are each configured to include a variable magnification lens system 401, an imaging lens 403, an image erecting prism 404, an eye width adjusting prism 405, a field diaphragm 406, and an eyepiece lens 407. Only the observation optical system for right eye 400R comprises a beam splitter 402.

The variable magnification lens system 401 is configured to include a plurality of zoom lenses 401a, 401b, 401c. Each zoom lens 401a, 401b, 401c is movable along the optical axes of the left and right observation optical systems O-400L, O-400R with a variable power mechanism. This alters the magnification in observing or imaging the subjects eye 8.

As shown in FIG. 2, the beam splitter 402 of the observation optical system for right eye 400R separates some of the observed light guided from the subjects eye 8 along the observation optical system for right eye and guides it towards the imaging optical system.

The imaging optical system is configured to include an imaging lens 1101, a reflecting mirror 1102, and a television camera 1103. The television camera 1103 is provided with an imaging element 1103*a*. The imaging element 1103*a* is configured with, for example, a CCD (Charge Coupled Devices) image sensor, a CMOS (Complementary Metal Oxide Semiconductor) image sensor, etc. As for the imaging element 1103*a*, one comprising a two-dimensional light reception plane (area sensor) is used.

The light reception plane of the imaging element 1103*a* is placed at the position optically conjugate to the front side focal position U0 of the objective lens 2.

The beam splitter and the imaging optical system may exist in the both right and left observation optical systems. It is possible to obtain a stereoscopic image by obtaining images having parallax at respective right and left imaging elements.

TV camera images can be used for obtaining an image of observation sites and also for tracking OCT observation sites. Although a mismatch occurs in a tomographic image obtained by the OCT if the subjects eye moves during OCT scanning due to an involuntary eye movement of the subjects eye, surgery operation, etc., it is possible to obtain tomographic images of the OCT without a mismatch by detecting the movement of the fundus based on the TV camera images and scanning the OCT optical system in accordance with this movement.

The image erecting prism 404 converts an inverted image to an erecting image. The eye width adjusting prism 405 is an optical element for adjusting the distance between right and left light paths depending on the eye width of an observer (distance between a left eye and a right eye). The field diaphragm 406 blocks a peripheral region in the cross section of the observed light to restrict the observer's field of view. The field diaphragm 406 is provided at the position conjugate to the front side focal position U0 of the objective lens 2 (the position of X).

The observation optical systems 400L, 400R may be configured to include a stereo variator configured to be removal from the light path of the observation optical system. The stereo variator is an optical axis position altering element for altering the relative position of the optical axes of the left and right observation optical systems O-400L, O-400R led respectively by the right and left variable magnification lens systems 401. The stereo variator is, for example, evacuated to the evacuation position provided on the observer side for the observed light path.

In the ophthalmologic microscope of the first embodiment, a sub-observation optical system 400S for an assistance observer to use is provided in addition to the observation optical system for a main observer to use.

As shown in FIG. 2, the sub-observation optical system 400S guides the return light (observed light) reflected/scattered at the subjects eye 8 which is being illuminated with the illuminating optical system, towards the eyepiece lens for assistant 411 by way of the objective lens 2. The optical axis of the sub-observation optical system is indicated by a dotted line O-400S in FIG. 2.

The sub-observation optical system 400S is also provided with a pair of right and left optical systems and capable of stereoscopic observation with the binocular.

As shown in FIG. 2, the sub-observation optical system 400S is configured to include a prism 408, a reflecting mirror 410, and an eyepiece lens for assistant 411. In the first embodiment, an imaging lens 409 is also placed between the prism 408 and the reflecting mirror 410. The observed light from the subject's eye 8 penetrates through the objective lens 2 and it is reflected by the reflecting surface 408*a* of the prism 408. The observed light reflected by the reflecting surface 408*a* penetrates through the imaging lens 409 and it is reflected by the reflecting mirror 410 and guided to the eyepiece lens for assistant 411.

The observation optical systems 400L, 400R and the sub-observation optical system 400S are accommodated in the ophthalmologic microscope body 6.

When observing a retina at the fundus of the eye, the front-end lens 14 is inserted onto optical axes O-400S, O-400L, O-400R right in front of the subjects eye by a moving means (not shown). In this case, the front side focal position U0 of the objective lens 2 is conjugate to the retina at the fundus of eye.

Also, when observing an anterior eye part such as a cornea, an iris, etc., the observation is performed by eliminating the front-end lens from right in front of the subjects eye.

FIG. 3 schematically illustrates the optical configuration of the OCT unit 10 used in the ophthalmologic microscope of the first embodiment.

The ophthalmologic device capable of executing an OCT of Fourier domain type is described herein. Particularly, the method of a swept source type OCT is applicable to the ophthalmologic device of the embodiment. The configuration of the present invention can be applied to the ophthalmologic device that can execute, for example, a spectral domain type OCT, other than swept source type.

As shown in FIG. 3, the OCT unit 10 constitutes an interferometer that divides the light emitted from the OCT light source unit 1001 into the measuring light LS and the reference light LR and detects interference between the measuring light LS and the reference light LR went through different light paths.

The OCT light source unit 1001 is configured to include a wavelength scanning (wavelength sweeping) light source capable of scanning (sweeping) the wavelength of the emitted light, similar to the general OCT device of the swept source type. The OCT light source unit 1001 changes the output wavelength temporally for the near infrared wavelength which is unrecognizable by human eyes. The light output from the OCT light source unit 1001 is indicated by a symbol LO.

The light (LO) output from the OCT light source unit 1001 is guided to the polarized wave controller 1003 by the optical fiber 1002 and adjusted its polarizing condition. The polarized wave controller 1003 adjusts the polarizing condition of the light LO guided within the optical fiber 1002 by applying stress to, for example, the loop-shaped optical fiber 1002, from outside.

The light LO whose polarizing condition has been adjusted by the polarized wave controller 1003 is guided to the fiber coupler 1005 by the optical fiber 1004 and divided into the measuring light LS and the reference light LR.

As shown in FIG. 3, the reference light LR is guided by an optical fiber 1006 to a collimator 1007 and converted into a parallel light flux. The reference light LR which became a parallel light flux is guided to a corner cube 1010 by way of a light path length correction member 1008 and a dispersion compensation member 1009. The light path length correction member 1008 functions as a delay mean for matching the light path lengths (optical distance) of the reference light LR and the measuring light LS. The dispersion compensation member 1009 functions as a dispersion compensation mean for matching the dispersion characteristics (optical distance) of the reference light LR and the measuring light LS.

The corner cube 1010 turns the reference light LR which was converted into a parallel light flux by the collimator 1007, from the advancing direction to the opposite direction.

The light path of the reference light LR incident on the corner cube 1010 and the light path of the reference light LR emitted from the corner cube 1010 are parallel. Also, the corner cube 1010 will be movable to the direction along the incident light path and the emitting light path of the reference light LR. This movement alters the length of the light path of the reference light LR (reference light path).

As shown in FIG. 3, the reference light LR through the corner cube 1010 goes through the dispersion compensation member 1009 and the light path length correction member 1008, enters the optical fiber 1012 after it is converted from a parallel light flux to a focused light flux by the collimator 1011, and it is guided to the polarized wave controller 1013 and adjusted its polarizing condition.

The polarized wave controller 1013 has a similar configuration to the polarized wave controller 1003, for example. The reference light LR whose polarizing condition has been adjusted by the polarized wave controller 1013 is guided to an attenuator 1015 by an optical fiber 1014 and adjusted its light volume under control of an arithmetic control unit 12. The reference light LR whose light volume has been adjusted by the attenuator 1015 is guided to a fiber coupler 1017 by an optical fiber 1016.

As seen from FIGS. 1 and 3, the measuring light LS generated by the fiber coupler 1005 is guided to the collimating lens 502 by the optical fiber 501. As shown in FIG. 1, the measuring light incident on the collimating lens 502 is irradiated towards the subjects eye 8 by way of the illuminating field diaphragm 509, the scanner mirrors 503a, 503b, the relay optical system 504, the first lens group 505, the reflecting mirror 508, the second lens group 506, and the objective lens for OCT 507. The measuring light is reflected/scattered at various depth positions of the subjects eye 8. The measuring light backscattered from the subjects eye 8 travels backwards the same pathway as the forward route and it is guided by the fiber coupler 1005 to reach the fiber coupler 1017 by way of the optical fiber 1018, as shown in FIG. 3.

The fiber coupler 1017 synthesizes (causes the interference between) the measuring light LS incident through the optical fiber 1018 and the reference light LR incident through the optical fiber 1016 to generate an interfering light. The fiber coupler 1017 generates a pair of interfering lights LC by branching the interfering light of the measuring light LS and the reference light LR at a predetermined branching ratio (for example, 50:50). The pair of interfering lights emitted from the fiber coupler 1017 is guided to a detector 1021 by two optical fibers 1019, 1020, respectively.

The detector 1021 is, for example, a Balanced Photo Diode (hereinafter, referred as "BPD") that comprises a pair of photodetectors for detecting a pair of interfering lights LC respectively and thereby outputs a difference of detection results. The detector 1021 sends the detection result (detection signal) to the arithmetic control unit 12. The arithmetic control unit 12 forms cross-sectional images by applying the Fourier transformation, etc. to the spectral distribution based on the detection result obtained by the detector 1021, for example, for each of a series of wavelength scanning (per A line). The arithmetic control unit 12 causes a displaying portion 13 to display the formed image.

Although the Michelson interferometer is employed in this embodiment, it is possible to appropriately employ any type of interferometer, for example, Mach-Zehnder, etc.

FIG. 4 schematically illustrates a shape of an objective lens used for the ophthalmologic microscope of the first embodiment of the present invention. FIG. 4 (A) illustrates an objective lens seen from the optical axis direction and FIG. 4 (B) is a cross-sectional view in the plane including a line AA' of FIG. 4 (A).

As shown in FIG. 4 (A), the objective lens 2 used in the first embodiment has a shape of circular lens with a hole 201 in its center. And the light path of the OCT optical system P-500 passes through that hole. And in the ophthalmologic microscope of the first embodiment, the light path of the observation optical system for left eye P-400L, the light path of the observation optical system for right eye P-400R, and the light path of the illuminating optical system P-300 respectively penetrates through different sections of the objective lens 2. Also, although not shown, the light path of the sub-observation optical system penetrates through in the proximity of the light path of the observation optical system for left eye P-400L.

Next, as shown in FIG. 4 (B), the sectional shape of the objective lens 2 has a shape of a convex lens with a hole in its center.

1-3. Shape of Objective Lens

Although a circular lens can be used as an objective lens for the ophthalmologic microscope of the present invention, it is preferable to decrease the angle formed by the optical axis of the OCT optical system and the optical axis of the observation optical system, and for this purpose the objective lens having a partial shape of circular lens or the objective lens having a shape of circular lens with a cutout or hole is preferably used.

In the present invention, "partial shape of circular lens" refers to a shape of circular lens which has been partially cut away in a plane view from the optical axis direction of the lens, and for example, but not limited to, the lens having a shape cut into a semicircular shape, a fan shape, a rectangular shape, etc. so that the light path of the observation optical system for left eye and the light path of the observation optical system for right eye penetrate through can be used.

Also, in the present invention, "shape of circular lens with a cutout or hole" refers to a shape with a cutout or hole in a plane view from the optical axis direction of the lens, and for example, but not limited to, the lens having a shape provided with a cutout or hole in a portion through which the light path of the OCT optical system penetrates can be used.

To ensure enough space to place optical elements of the OCT optical system, etc., the objective lens having a partial shape of circular lens is preferably used, rather than providing the circular lens with a cutout or hole.

Using a lens with such shape, the light path of the OCT optical system can pass through the cutaway portion where there is no lens exist in a circular lens, or through the cutout or hole provided in the lens. This allows to decrease the angle formed by the optical axis of the OCT optical system and the optical axis of the observation optical system without the optical axis of the OCT optical system penetrating through the objective lens.

In the present invention, the angle formed by the optical axis of the OCT optical system and the optical axis of the observation optical system (either of optical axes of the right and left observation light paths) may be preferably between 1 and 15°, more preferably between 4 and 10°, and yet preferably between 6 and 8°.

In the ophthalmologic microscope of the present invention, a circular lens or a lens consisting of part of a circular lens can be divided into two, and one of the divided lenses can be an objective lens through which the optical axis of the observation optical system penetrates and the other one of the divided lenses can be objective lens through which the optical axis of the OCT optical system penetrates.

Here, "lens consisting of part of a circular lens" can use lens having a "partial shape of circular lens" described above.

By using the divided lenses like this and making each of their positions independently controllable, it is possible to control the observation optical system and the OCT optical system independently.

1-4. Second Embodiment

Preferably, the OCT optical system can be additionally incorporated as an extension function into the ophthalmologic microscope comprising an observation optical system and an illuminating optical system. To additionally incorporate in this way, the inventors found that it can be compactly incorporated by bending the light path of the OCT optical system twice to adapt to the original function of the microscope.

That is, in the ophthalmologic microscope of the present invention, it is preferable that the OCT optical system comprises:

a first optical member that guides a light from an OCT light source to a first optical axis direction;

a first reflecting member that guides the light guided to the first optical axis direction to a second optical axis direction substantially perpendicular to the first optical axis direction;

a second optical member that relays the light guided to the second optical axis direction; and a second reflecting member that guides the light relayed by the second optical member to a third optical axis direction substantially perpendicular to the second optical axis direction, wherein an objective lens for OCT is placed on the third optical axis so that it can irradiate a prescribed section of the subject's eye with the light guided to the third optical axis direction.

With this optical configuration, the OCT optical system can be compactly incorporated by adapting to the original function of the ophthalmologic microscope.

Hereinafter, examples of the embodiments of the ophthalmologic microscope of the present invention comprising the OCT optical system whose light path has been bended twice will be fully described in reference to drawings.

FIGS. 5 to 10 schematically illustrate the second embodiment which is an example of the ophthalmologic microscope of the present invention.

Figure 5:
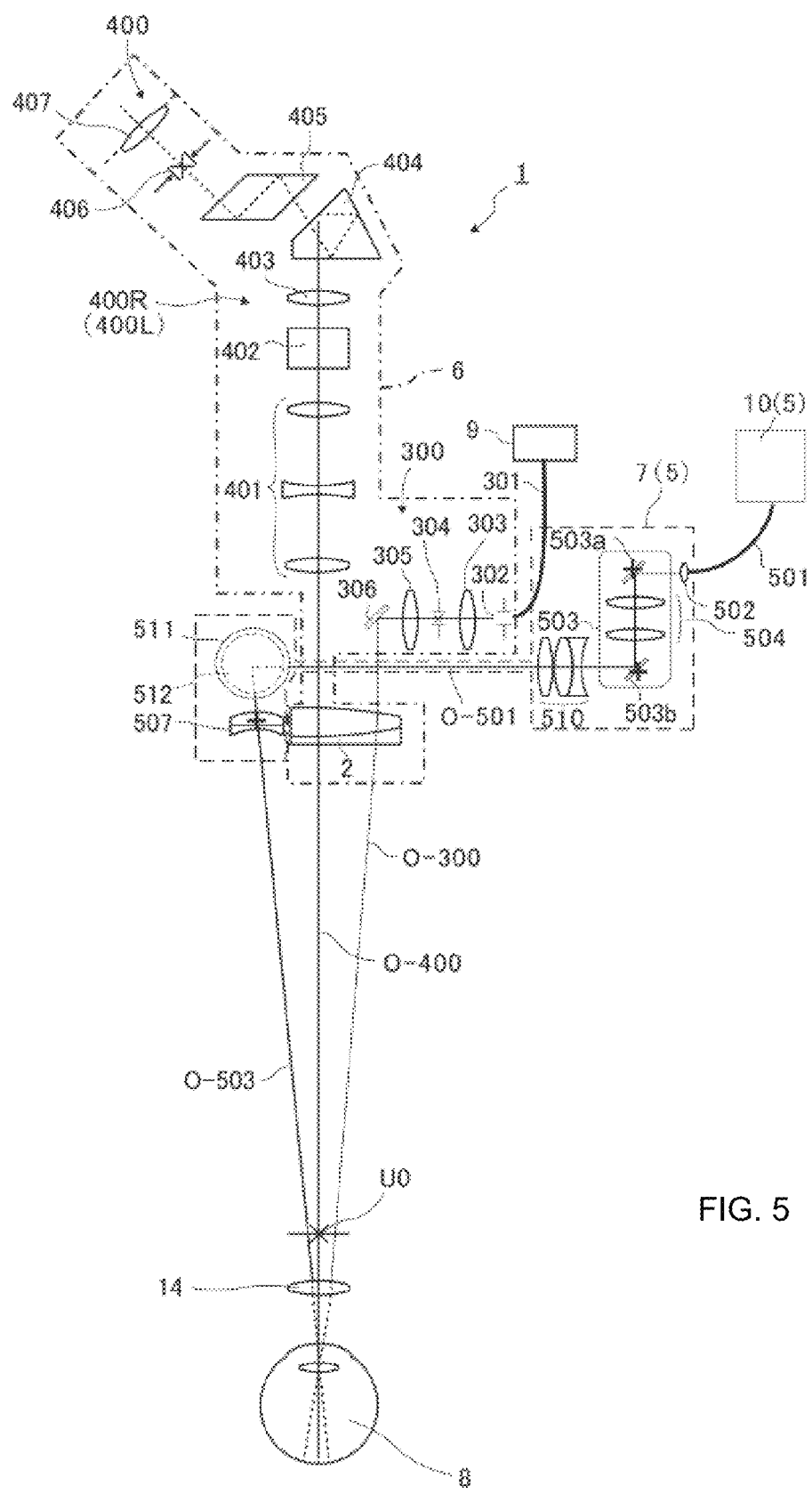
FIG. 5 schematically illustrates the configuration of an optical system taken from a side view, regarding to the ophthalmologic microscope of the second embodiment of the present invention.
Figure 6:
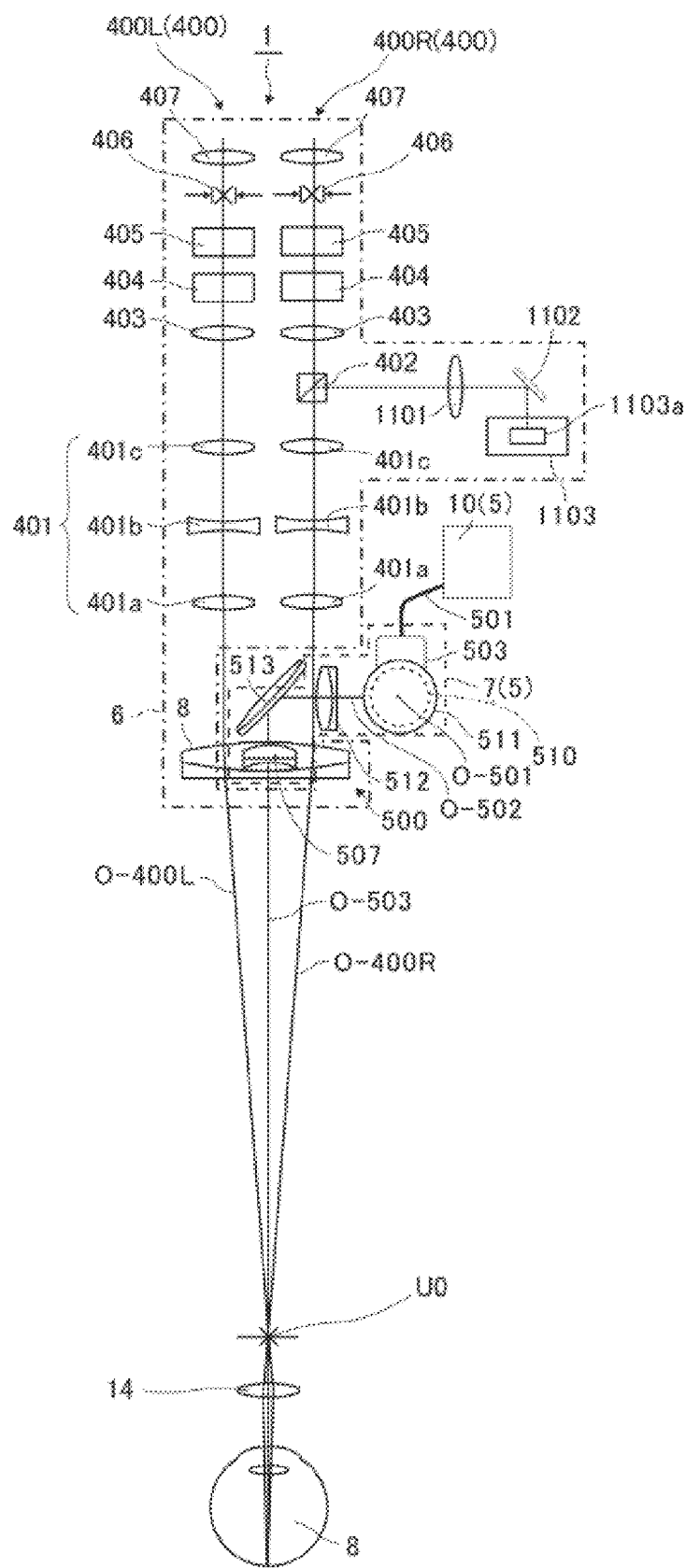
FIG. 6 schematically illustrates the configuration of an optical system taken from a front view, regarding to the ophthalmologic microscope of the second embodiment of the present invention.

FIG. 5 is a side schematic view of the ophthalmologic microscope 1, and FIG. 6 is a front schematic view of the same.

As shown in FIGS. 5 and 6, an OCT device 5 is arranged along with the ophthalmologic microscope 1.

The ophthalmologic microscope 1 is provided with an illuminating optical system 300 (not shown in FIG. 6), an observation optical system 400, and an OCT optical system 500.

The observation optical system 400 can observe a prescribed section of the observation object (subjects eye 8 in FIGS. 5 and 6). As referenced in FIG. 5, the illuminating optical system 300 can illuminate a part of the subjects eye 8 to be observed.

The OCT device 5 arranged along with the ophthalmologic microscope 1 can obtain tomographic images of the subjects eye 8. The OCT optical system 500 is incorporated into the ophthalmologic microscope 1 as a part of the OCT device 5. The round-trip guide light path of the measuring light is constructed by the OCT optical system 500, the front-end lens 14, and the reflecting surface of the subjects eye 8 (cornea, retina, etc.).

As specified in FIG. 6, the observation optical system 400 comprises an observation optical system for right eye 400R and an observation optical system for left eye 400L. In FIG. 5, the entire configuration is shown for the observation optical system for right eye 400R, while only the objective lens 2 to be shared with the observation optical system for right eye 400R is shown for the observation optical system for left eye 400L.

Also, as specified in FIG. 6, the optical axis O-400R of the observation optical system for right eye 400R and the optical axis O-400L of the observation optical system for left eye 400L respectively pass through the objective lens 2.

In this embodiment, the illuminating optical system 300 and the observation optical system 400 are accommodated in an ophthalmologic microscope body 6. Also, the OCT optical system 500 is accommodated in a function expansion unit 7. In FIGS. 5 and 6, the ophthalmologic microscope body 6 is indicated by a dashed-dotted line and the function expansion unit 7 is indicated by a dashed line.

The function expansion unit 7 is removably coupled to the ophthalmologic microscope body 6 via a joint (not shown).

As shown in FIGS. 5 and 6, the OCT device 5 consists of an OCT unit 10 and a function expansion unit 7.

The function expansion unit 7 accommodates an OCT optical system 500.

Figure 7:
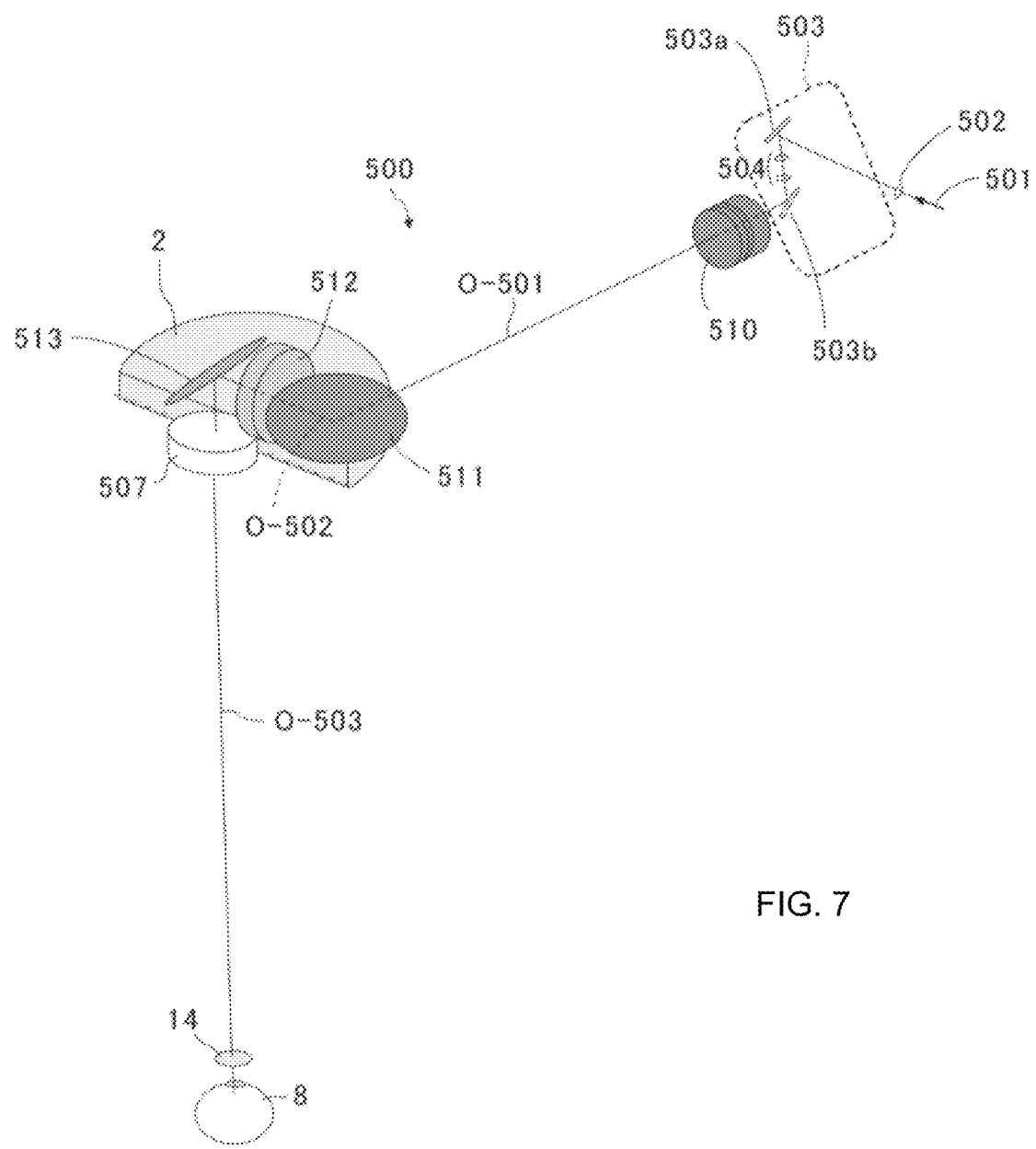
FIG. 7 is a perspective view of an OCT optical system, regarding to the ophthalmologic microscope of the second embodiment of the present invention.
Figure 8:
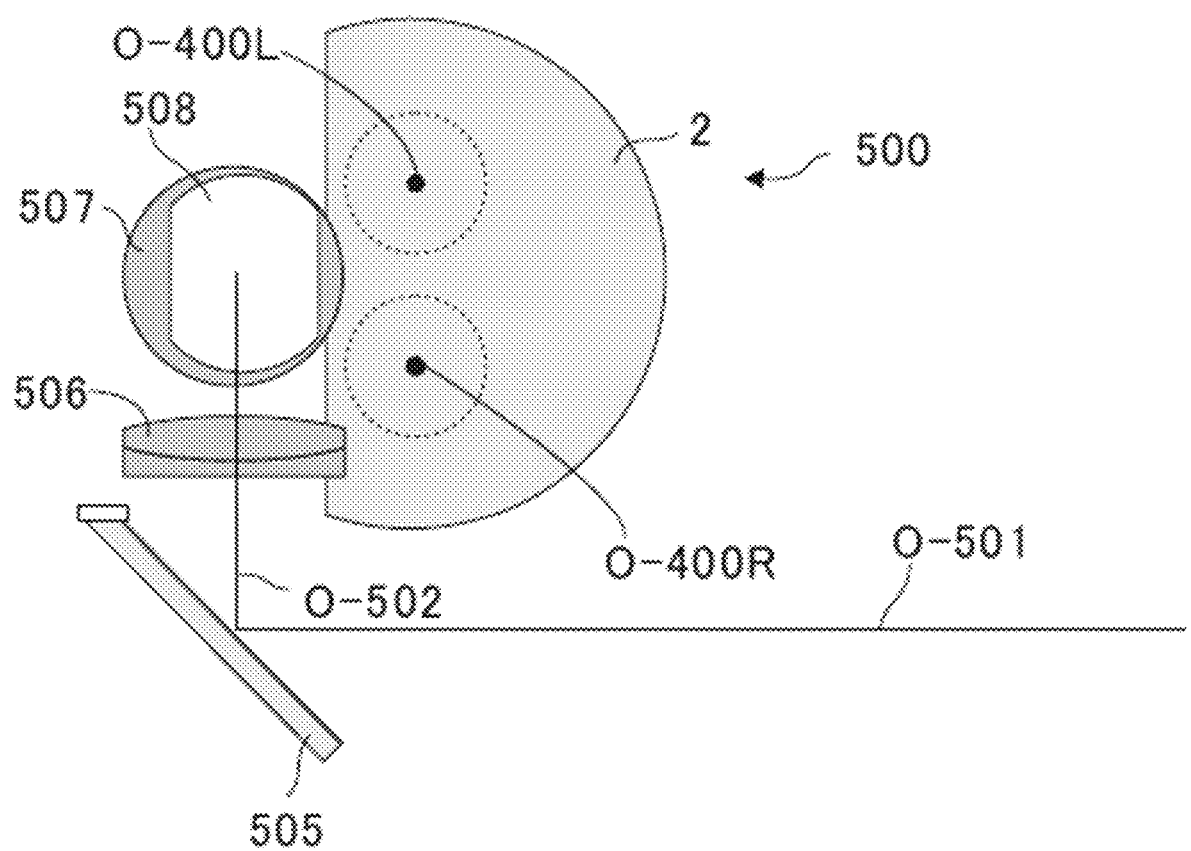
FIG. 8 is a plane view of an OCT optical system shown in FIG. 7, regarding to the ophthalmologic microscope of the second embodiment of the present invention.
Figure 9:
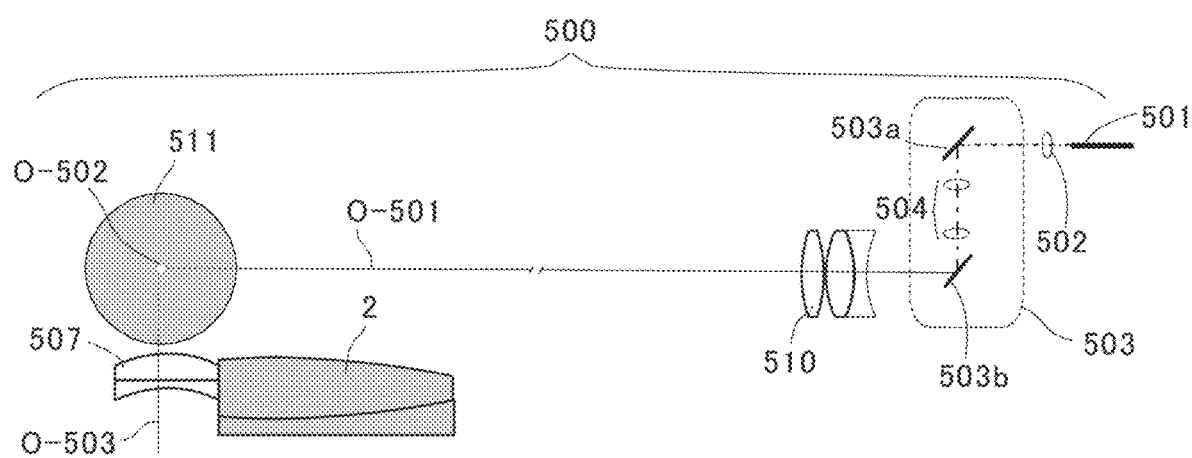
FIG. 9 is a side view of an OCT optical system shown in FIG. 7, regarding to the ophthalmologic microscope of the second embodiment of the present invention.
Figure 10:
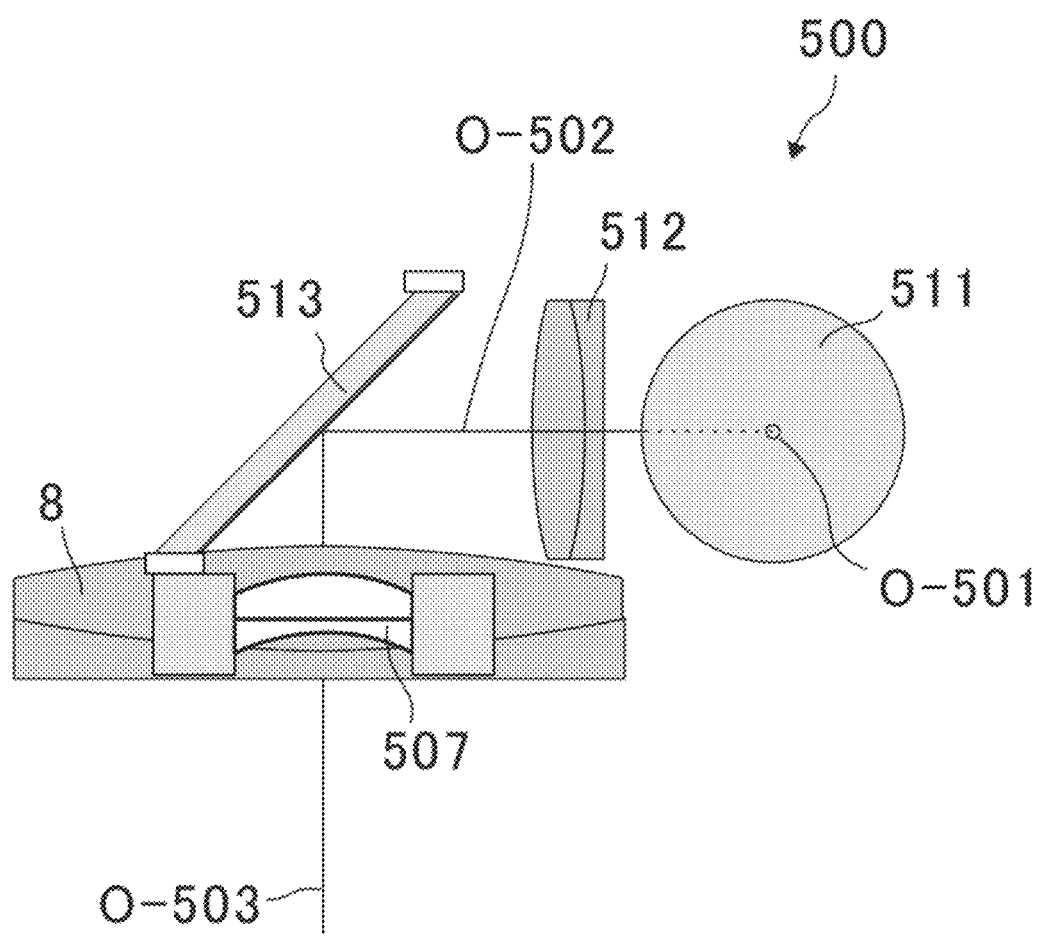
FIG. 10 is a front view of an OCT optical system shown in FIG. 7, regarding to the ophthalmologic microscope of the second embodiment of the present invention.

FIG. 7 is a perspective view of the OCT optical system 500, FIG. 8 is a plane view of the same, FIG. 9 is a side view of the same, and FIG. 10 is a front view of the same. However, in FIGS. 8 and 10, a collimating lens 502, a scanning function part 503, and a first optical member 510 (described below) are not shown.

In FIGS. 7 and 9, the OCT optical system 500 is configured to include a collimating lens 502, a scanning function part 503, a first optical member 510, a first reflecting member 511, a second optical member 512, a second reflecting member 513, and an objective lens for OCT 507.

The scanning function part 503 is a two-dimensional scanning mechanism that comprises scanning mirrors 503a, 503b. The scanning function part 503 is provided at the back side of the ophthalmologic microscope body 6 (the far side from an observer).

The first optical member 510 is an OCT imaging lens that guides a light scanned by the scanning function part 503 to a direction of the first optical axis O-501. The first optical axis O-501 is formed from the far side to the near side at the position near the right outer side of the ophthalmologic microscope body 6 when viewing it from the front, and the light scanned by the scanning function part 503 is guided on the first optical axis O-501 from the far side to the near side.

Here, as shown in FIGS. 5, 7, and 9, both of the first scanning mirror 503a and the second scanning mirror 503b can be in a substantially optically conjugate positional relation with the objective lens for OCT 507 by providing a relay optical system 504 between the first scanning mirror 503a and the second scanning mirror 503b. In FIG. 5, the sections in an optically conjugate positional relation are indicated by symbol +.

Having such conjugate positional relation, similarly to the first embodiment, it is possible to reduce the restriction imposed by the size (aperture) of the objective lens for OCT 507 and to have a wide irradiation region even with an objective lens for OCT of small aperture.

As shown in FIGS. 7, 8, 9, and 10, the light guided on the first optical axis O-501 is guided to the direction of a second optical axis O-502 perpendicular to the direction of the first optical axis O-501 by the first reflecting member 511.

In this embodiment, as shown in FIG. 6, the second optical axis O-502 is formed so as to face inward from the right outer side of the ophthalmologic microscope body 6.

The second optical member 512 is placed on the second optical axis O-502, and the light passed through the second optical member 512 is reflected downward (direction substantially perpendicular to the second optical axis O-502) by the second reflecting member 513. This reflecting light path is indicated by the third optical axis direction O-503.

In this embodiment, the objective lens 2 has a partial shape of circular lens which has been cut away to have a cutting plane substantially parallel to the optical axis O-400, as shown in FIG. 5.

In this embodiment, the objective lens for OCT 507 is accommodated in the cutaway portion of this circular lens.

The light guided by the third optical axis direction O-503 is focused at a predetermined position on a side of the subjects eye 8 by the objective lens for OCT 507.

In FIGS. 5 and 6, the front side focal position U0 of the objective lens 2 is located before the subjects eye 8 and the front-end lens 14 is placed between the subjects eye 8 and the front side focal position U0.

The front-end lens 14 is a lens used when observing a retina at the fundus of the eye, and it is inserted onto optical axes O-300, O-400L, O-400R, O-503 right in front of the subjects eye by moving means not shown. In this case, the front side focal position U0 of the objective lens 2 is conjugate to the retina at the fundus of eye. Also, when observing an anterior eye part such as a cornea, an iris, etc., the observation is performed by eliminating the front-end lens 14 from right in front of the subjects eye 8.

As described above, the optical axis O-503 of the OCT optical system 500 passes through the objective lens for OCT 507 and it is away from the optical axis O-400 of the observation optical system 400.

Therefore, the OCT optical system 500 and the observation optical system 400 are independent of each other.

1-5. Third Embodiment

Figure 11A:
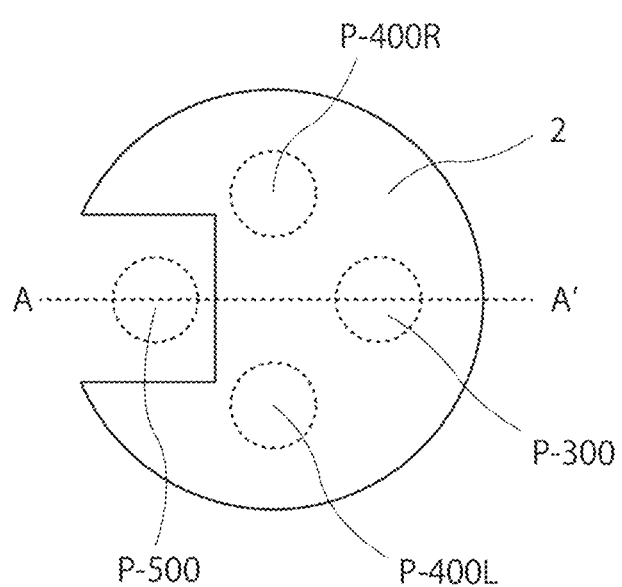
FIG. 11 schematically illustrates a shape of an objective lens used for the ophthalmologic microscope of the third embodiment of the present invention.
Figure 11B:
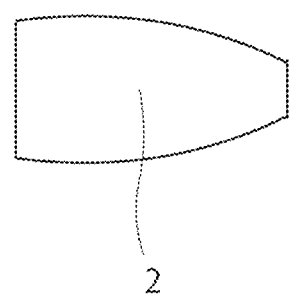

A shape of an objective lens used in the third embodiment which is other example of the ophthalmologic microscope of the present invention is shown in FIG. 11. FIG. 11 (A) illustrates an objective lens seen from the optical axis direction and FIG. 11 (B) is a cross-sectional view in the plane including a line AA' of FIG. 11 (A).

As shown in FIG. 11 (A), the objective lens 2 used in the third embodiment has a shape of circular lens with a partial cutout. And, the light path of the OCT optical system P-500 passes through that cutout portion.

Also, as shown in FIG. 11 (B), the sectional shape of the objective lens 2 has a partial shape of convex lens which has been partially cut away.

1-6. Fourth Embodiment

A shape of an objective lens used in the fourth embodiment which is other example of the ophthalmologic microscope of the present invention is shown in FIG. 12. FIG. 12 (A) illustrates an objective lens seen from the optical axis direction and FIG. 12 (B) is a cross-sectional view of in the plane including a line AA' FIG. 12 (A).

As shown in FIG. 12 (A), the objective lens 2 used in the fourth embodiment has a shape of circular lens which has been partially cut away in a rectangular shape, and the light path of the observation optical system for left eye P-400L and the light path of observation optical system for right eye P-400R respectively penetrate through different sections of the objective lens 2. And the light path of the OCT optical system P-500 and the light path of the illuminating optical system P-300 pass through in the proximity of the objective lens 2.

Also, as shown in FIG. 12 (B), the sectional shape of the objective lens 2 has a partial shape of convex lens which has been partially cut away.

1-7. Fifth Embodiment

Figure 13A:
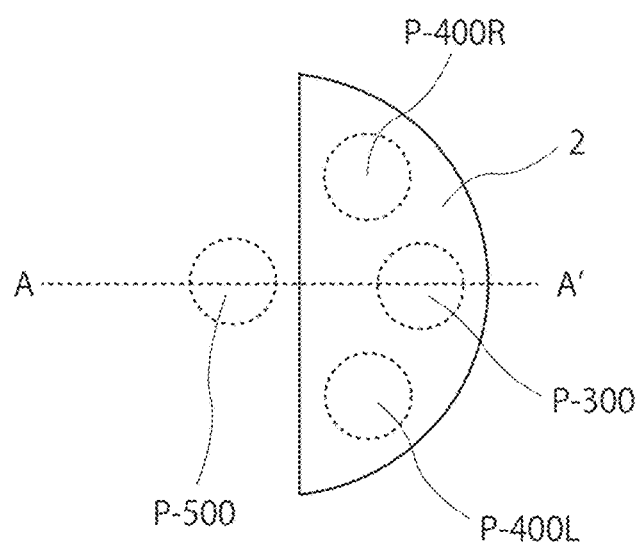
FIG. 13(A) is a view from the direction of the optical axis of the objective lens and FIG. 13 (B) is a cross-sectional view in the plane including a line AA' of FIG. 13 (A).
Figure 13B:
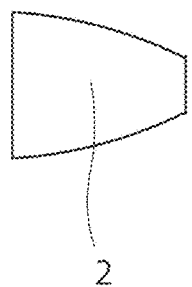
FIG. 13 schematically illustrates a shape of objective lens used for the ophthalmologic microscope of the fifth embodiment of the present invention.

A shape of an objective lens used in the fifth embodiment which is other example of the ophthalmologic microscope of the present invention is shown in FIG. 13. FIG. 13 (A) illustrates an objective lens seen from the optical axis direction and FIG. 13 (B) is a cross-sectional view in the plane including a line AA' of FIG. 13 (A).

As shown in FIG. 13 (A), the objective lens 2 used in the fifth embodiment has a shape of circular lens which has been partially cut away in a semicircular shape, and the light path of the observation optical system for left eye P-400L, the light path of the observation optical system for right eye P-400R, and the light path of the illuminating optical system P-300 respectively penetrate through different sections of the objective lens 2. And the light path of the OCT optical system P-500 passes through in the proximity of the objective lens 2.

Also, as shown in FIG. 13 (B), the sectional shape of the objective lens 2 has a partial shape of convex lens which has been partially cut away.

1-8. Sixth Embodiment

Figure 14A:
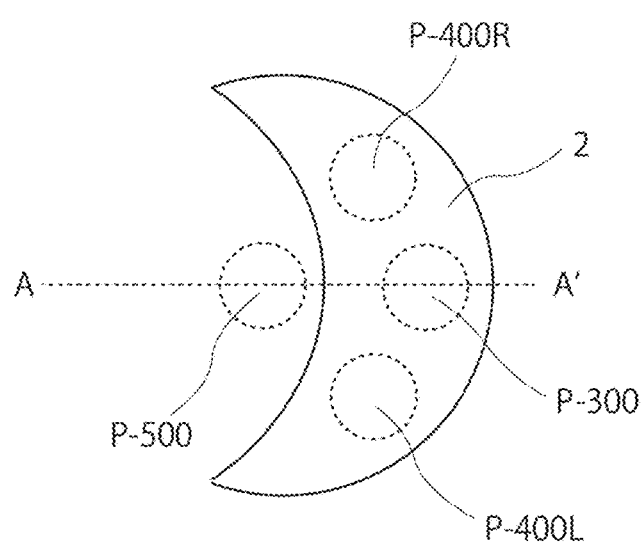
FIG. 14 schematically illustrates a shape of an objective lens used for the ophthalmologic microscope of the sixth embodiment of the present invention.
Figure 14B:
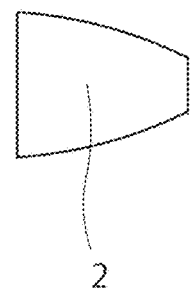
Figure 16:
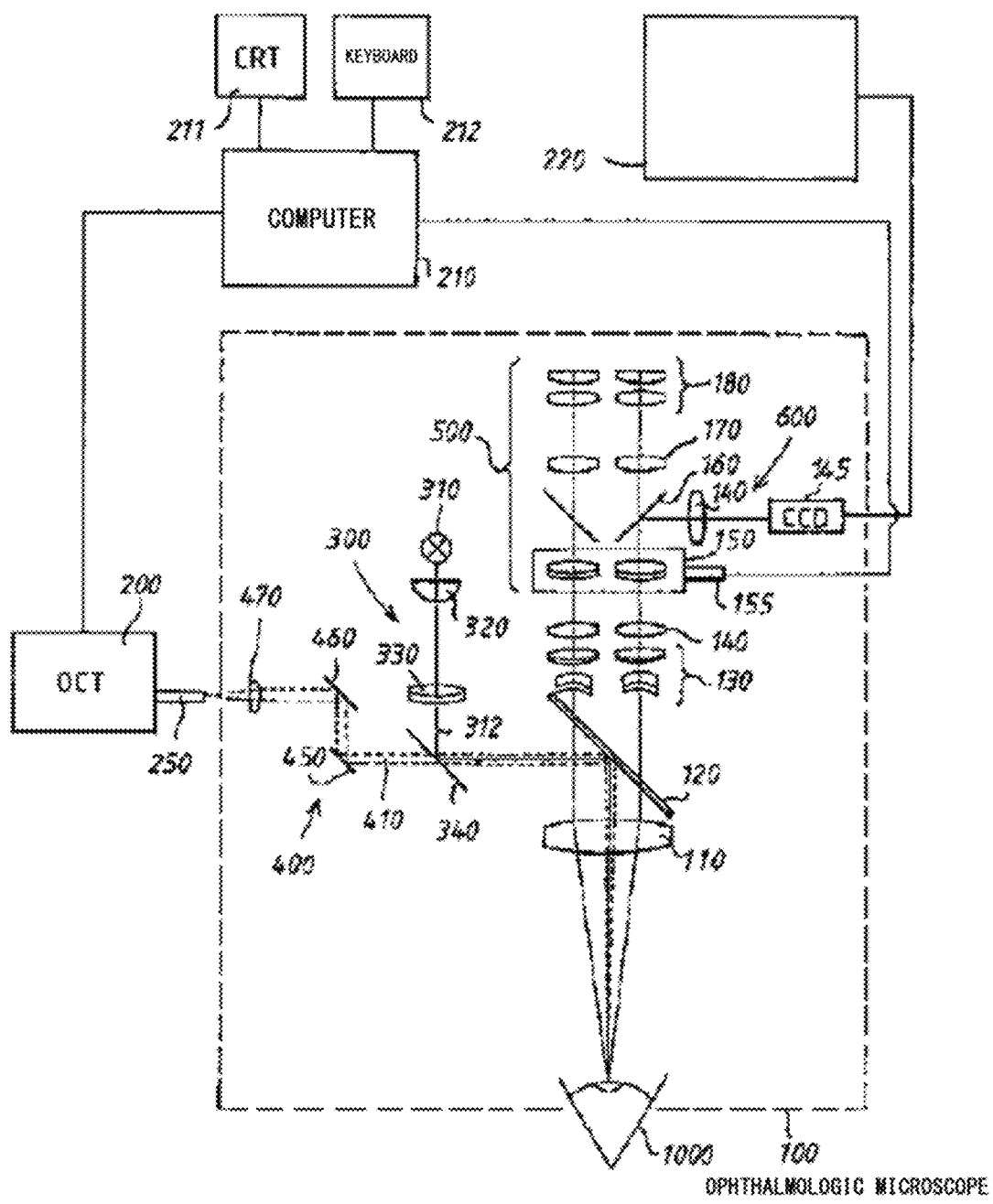
FIG. 16 is a drawing cited from FIG. 1 of Patent document 1.
Figure 17:
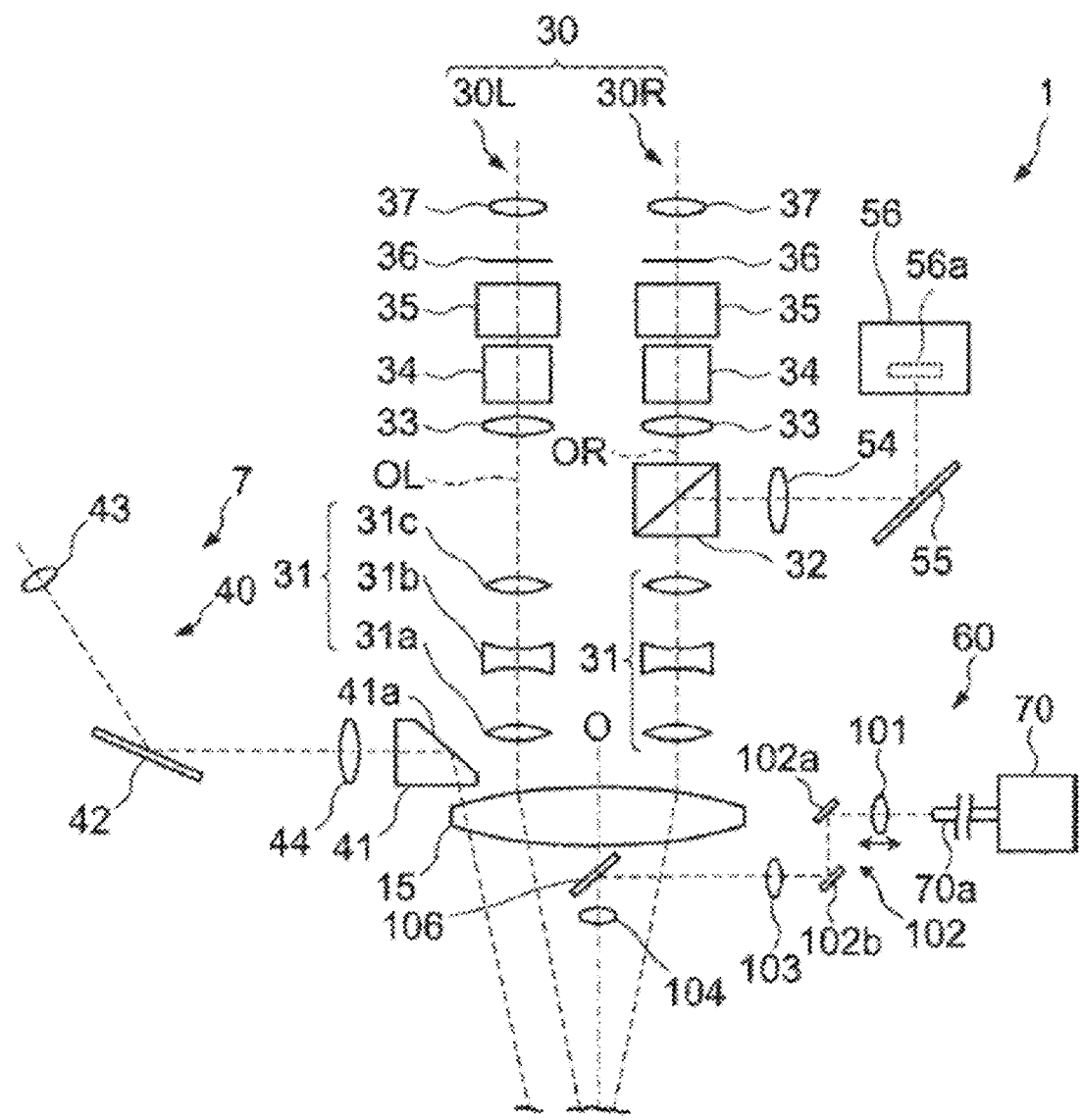
FIG. 17 is a drawing cited from FIG. 3 of Patent document 7.

A shape of an objective lens used in the sixth embodiment which is other example of the ophthalmologic microscope of the present invention is shown in FIG. 14. FIG. 14 (A) illustrates an objective lens seen from the optical axis direction and FIG. 14 (B) is a cross-sectional view in the plane including a line AA' of FIG. 14 (A).

As shown in FIG. 14 (A), the objective lens 2 used in the sixth embodiment has a shape of circular lens which has been partially cut away in a crescentic shape, and the light path of the observation optical system for left eye P-400L, the light path of the observation optical system for right eye P-400R, and the light path of the illuminating optical system P-300 respectively penetrate through different sections of the objective lens 2. And the light path of the OCT optical system P-500 passes through in the proximity of the objective lens 2.

Also, as shown in FIG. 14 (B), the sectional shape of the objective lens 2 has a partial shape of convex lens which has been partially cut away.

1-9. Seventh Embodiment

Shapes of an objective lens and an objective lens for OCT used in the seventh embodiment which is other example of the ophthalmologic microscope of the present invention is shown in FIG. 15. FIG. 15 (A) illustrates an objective lens seen from the optical axis direction and FIG. 15 (B) is a cross-sectional view in the plane including a line AA' of FIG. 15 (A).

As shown in FIG. 15 (A), the objective lens and the objective lens for OCT used in the seventh embodiment is a circular lens divided in two. One of the divided lenses 2 is used as an objective lens, through which the light path of the observation optical system for left eye P-400L, the light path of the observation optical system for right eye P-400R, and the light path of the illuminating optical system P-300 penetrate. The other one of the divided lenses 507 is used as an objective lens for OCT, through which the light path of the OCT optical system P-500 penetrates.

Also, as shown in FIG. 15 (B), the sectional shape of the objective lens 2 and the objective lens for OCT 507 is a shape of convex lens divided in two.

2. Function Expansion Unit

The function expansion unit of the present invention is attachable to and detachable from the ophthalmologic microscope and capable of adding functions of the OCT to the ophthalmologic microscope.

The function expansion unit of the present invention is used for an ophthalmologic microscope comprising an illuminating optical system for illuminating a subjects eye, an observation optical system that comprises the light path of an observation optical system for left eye and the light path of an observation optical system for right eye to observe the subjects eye illuminated by the illuminating optical system, and an objective lens through which the optical axis of the observation optical system for left eye and the optical axis of the observation optical system for right eye of the observation optical system commonly penetrate.

And, the function expansion unit of the present invention comprises a joint attachable to and detachable from the ophthalmologic microscope, and an OCT optical system comprising a light path of a measuring light for testing the subject's eye by Optical Coherence Tomography, a deflection optical element that scans the measuring light, and an objective lens for OCT, characterized in that the optical axis of the OCT optical system does not penetrate through the objective lens but penetrates through the objective lens for OCT when the function expansion unit is attached to the ophthalmologic microscope via the joint, and the deflection optical element and the objective lens for OCT are in a substantially optically conjugate positional relation.

The OCT optical system for the function expansion unit of the present invention is independent from the observation optical system for the ophthalmologic microscope, thereby allows for unitization and is effective in increasing the degree of freedom in the optical design. Also, as the function expansion unit of the present invention is attachable to and detachable from the ophthalmologic microscope via a joint, it is effective in readily adding functions of the OCT to the ophthalmologic microscope.

"Joint" in the function expansion unit of the present invention is not particularly limited as long as it makes the function expansion unit attachable to and detachable from the ophthalmologic microscope, and can be, for example, but not limited to, a joint for coupling by a fitting or a joint for coupling by using a screw.

A concrete example of the function expansion unit of the present invention is as described as the function expansion unit in the ophthalmologic microscope of the first embodiment and the ophthalmologic microscope of the second embodiment (portion indicated by the symbol 7 in FIGS. 1 and 6 which is surrounded by the dashed-dotted lines).

3. Function Expansion Set

The function expansion set of the present invention is a set including the function expansion unit described in 2 above and the objective lens for replacement for replacing objective lens of the ophthalmologic microscope. Here, the objective lens having a shape described in 1-3 above can be used as an objective lens for replacement. A concrete example of the objective lens for replacement can include the objective lens used in the first embodiment and the third or seventh embodiment above (FIGS. 4 and 11-15).

With the function expansion set of the present invention is, since the function expansion unit can be attached to and detached from the ophthalmologic microscope via a joint, it is effective in readily adding functions of the OCT to the ophthalmologic microscope.

INDUSTRIAL APPLICABILITY

The ophthalmologic microscope, the function expansion unit, the function expansion set of the present invention are useful in the industry of manufacturing ophthalmic medical equipment.

EXPLANATION OF SYMBOLS

Symbols used in FIGS. 1-15 will be explained below:
1 ophthalmologic microscope
2 objective lens
201 hole in objective lens
300 illuminating optical system
301 optical fiber
302 emitted light diaphragm
303 condenser lens
304 illuminating field diaphragm
305 collimating lens
306 reflecting mirror
400 observation optical system
400L observation optical system for left eye
400R observation optical system for right eye
400S sub-observation optical system
401 variable magnification lens system
401$a$, 401$b$, 401$c$ zoom lens
402 beam splitter
403 imaging lens
404 image erecting prism
405 eye width adjusting prism
406 field diaphragm
407 eyepiece lens
408 prism
408$a$ reflecting surface of prism
409 imaging lens
410 reflecting mirror
411 eyepiece lens for assistant
5 OCT device
500 OCT optical system
501 optical fiber
502 collimating lens
503 scanning function part
503$a$, 503$b$ scanning mirror
504 relay optical system
505 first lens group
506 second lens group
507 objective lens for OCT
508 reflecting mirror
509 illuminating field diaphragm
510 first optical member
511 first reflecting member
512 second optical member 513 second reflecting member
6 ophthalmologic microscope body
7 function expansion unit
8 subjects eye
9 illuminating light source
20 OCT unit
1001 OCT light source unit
1002 optical fiber
1003 polarized wave controller
1004 optical fiber
1005 fiber coupler
1006 optical fiber
1007 collimator
1008 light path length correction member
1009 dispersion compensation member
1010 corner cube
1011 collimator
1012 optical fiber
1013 polarized wave controller
1014 optical fiber
1015 attenuator
1016 optical fiber
1017 fiber coupler
1018 optical fiber
1019 optical fiber
1020 optical fiber
1021 detector
1101 imaging lens
1102 reflecting mirror
1103 television camera
1103a imaging element
12 arithmetic control unit
13 displaying portion
14 front-end lens
O-300 optical axis of illuminating optical system
O-400 optical axis of observation optical system
O-400L optical axis of observation optical system for left eye
O-400R optical axis of observation optical system for right eye
O-400S optical axis of sub-observation optical system
O-500 optical axis of OCT optical system
O-501 first optical axis
O-502 second optical axis
O-503 third optical axis
P-300 light path of illuminating optical system
P-400L light path of observation optical system for left eye
P-400R light path of observation optical system for right eye
P-500 light path of OCT optical system
LO light output from OCT light source unit
LC interfering light
LS measuring light
LR reference light
U0 front side focal position

The invention claimed is:

1. An ophthalmologic microscope comprising:
an illuminating optical system for illuminating a subject's eye;
an observation optical system comprising an observation optical system for left eye and an observation optical system for right eye to observe the subject's eye illuminated by the illuminating optical system;
an objective lens through which an optical axis of the observation optical system for left eye and an optical axis of the observation optical system for right eye of the observation optical system commonly penetrate; and
an OCT optical system comprising a light path of a measuring light for testing the subject's eye by Optical Coherence Tomography, a deflection optical element that scans the measuring light, and an objective lens for OCT through which the optical axis of the OCT optical system penetrates;
wherein the observation optical system, the objective lens, and the OCT optical system are placed in such a way that the optical axis of the OCT optical system does not penetrate through the objective lens through which the optical axis of the observation optical system penetrates,
wherein the deflection optical element and the objective lens for OCT are in a substantially optically conjugate positional relation, and
wherein the objective lens has a partial shape of circular lens or a shape of circular lens with a cutout or hole,
wherein the optical axis of the OCT optical system penetrates through a portion where the objective lens does not exist, or through the cutout or hole provided in the objective lens.

2. The ophthalmologic microscope according to claim 1, the OCT optical system further comprising:
a first optical member that guides a light from an OCT light source to a first optical axis direction;
a first reflecting member that guides the light guided to the first optical axis direction to a second optical axis direction substantially perpendicular to the first optical axis direction;
a second optical member that relays the light guided to the second optical axis direction;
a second reflecting member that guides the light relayed by the second optical member to a third optical axis direction substantially perpendicular to the second optical axis direction,
wherein the objective lens for OCT is placed on the third optical axis so that it can irradiate a prescribed section of the subject's eye with the light guided to the third optical axis direction.

3. The ophthalmologic microscope according to claim 1, wherein:
the deflection optical element comprises a pair of two deflection optical elements that scan in a different direction,
the deflection optical element comprises a relay optical system on a light path between the two deflection optical elements, and
both of the two deflection optical elements are in a substantially optically conjugate positional relation with the objective lens for OCT.

4. The ophthalmologic microscope according to claim 1, further comprising an objective lens position control mechanism that adjusts a position of the objective lens or the objective lens for OCT.

5. The ophthalmologic microscope according to claim 1, wherein the OCT optical system is detachably unitized.

6. The ophthalmologic microscope according to claim 1, further comprising a detachable front-end lens onto a light path between the subject's eye and the objective lens to observe a retina of the subject's eye.

7. An ophthalmologic microscope comprising:
an illuminating optical system for illuminating a subject's eye;
an observation optical system comprising an observation optical system for left eye and an observation optical system for right eye to observe the subject's eye illuminated by the illuminating optical system;

an objective lens through which an optical axis of the observation optical system for left eye and an optical axis of the observation optical system for right eye of the observation optical system commonly penetrate; and an OCT optical system comprising a light path of a measuring light for testing the subject's eye by Optical Coherence Tomography, a deflection optical element that scans the measuring light, and an objective lens for OCT through which the optical axis of the OCT optical system penetrates;

wherein the observation optical system, the objective lens, and the OCT optical system are placed in such a way that the optical axis of the OCT optical system does not penetrate through the objective lens through which the optical axis of the observation optical system penetrates, wherein the deflection optical element and the objective lens for OCT are in a substantially optically conjugate positional relation, and either a circular lens or a lens comprising part of a circular lens is divided in two, with one of the divided lenses being the objective lens and the other being the objective lens for OCT.

8. A function expansion set for an ophthalmologic microscope, comprising:

a function expansion unit comprising:
    an illuminating optical system for illuminating a subject's eye;
    an observation optical system that comprises an observation optical system for left eye and an observation optical system for right eye to observe the subject's eye illuminated by the illuminating optical system; and
    an objective lens through which the optical axis of the observation optical system for left eye and the optical axis of the observation optical system for right eye of the observation optical system commonly penetrate;
a joint attachable to and detachable from the ophthalmologic microscope; and
an OCT optical system comprising:
    a light path of a measuring light for testing the object's eye by Optical Coherence Tomography;
    a deflection optical element that scans the measuring light; and
    an objective lens for OCT,
    wherein, when attaching the function expansion unit to the ophthalmologic microscope via the joint, the optical axis of the OCT optical system does not penetrate through the objective lens but penetrates through the objective lens for OCT, and
    wherein the deflection optical element and the objective lens for OCT are in a substantially optically conjugate positional relation; and an objective lens for replacement to replace the objective lens wherein the objective lens for replacement has either a partial shape of circular lens or a shape of circular lens with a cutout or hole, wherein when replacing the objective lens with the objective lens for replacement and attaching the function expansion unit to the ophthalmologic microscope via the joint, the optical axis of the OCT optical system penetrates through a portion where the objective lens for replacement does not exist, or through the cutout or hole provided in the objective lens for replacement.

9. The function expansion set according to claim 8, the OCT optical system further comprising:

a first optical member that guides a light from an OCT light source to a first optical axis direction;

a first reflecting member that guides the light guided to the first optical axis direction to a second optical axis direction substantially perpendicular to the first optical axis direction;

a second optical member that relays the light guided to the second optical axis direction; and a second reflecting member that guides the light relayed by the second optical member to a third optical axis direction substantially perpendicular to the second optical axis direction, wherein the objective lens for OCT is placed on the third optical axis so that it can irradiate a prescribed section of the subject's eye with the light guided to the third optical axis direction.

10. The function expansion set according to claim 8, wherein:

the deflection optical element consists of a pair of two deflection optical elements that scan in a different direction, the deflection optical element comprises a relay optical system on a light path between the two deflection optical elements, and both of the two deflection optical elements are in a substantially optically conjugate positional relation with the objective lens for OCT.

11. The function expansion set according to claim 8, further comprising a detachable front-end lens onto a light path between the subject's eye and the objective lens to observe a retina of the subject's eye.

* * * * *